(12) United States Patent
Rothstein

(10) Patent No.: US 10,433,993 B2
(45) Date of Patent: Oct. 8, 2019

(54) VALVE PROSTHESIS HAVING A RADIALLY-EXPANDABLE SLEEVE INTEGRATED THEREON FOR DELIVERY AND PREVENTION OF PARAVALVULAR LEAKAGE

(71) Applicant: Medtronic Vascular, Inc., Santa Rosa, CA (US)

(72) Inventor: Paul Rothstein, Elk River, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 15/411,494

(22) Filed: Jan. 20, 2017

(65) Prior Publication Data
US 2018/0207011 A1    Jul. 26, 2018

(51) Int. Cl.
  *A61F 2/962*    (2013.01)
  *A61F 2/24*    (2006.01)
  *A61F 2/844*    (2013.01)

(52) U.S. Cl.
  CPC ............. *A61F 2/962* (2013.01); *A61F 2/24* (2013.01); *A61F 2/2439* (2013.01); *A61F 2/844* (2013.01);
  (Continued)

(58) Field of Classification Search
  CPC ...... A61F 2/962; A61F 2/2427–2/2439; A61F 2/95–2/97; A61F 2/24–2/2418
  (Continued)

(56) References Cited

U.S. PATENT DOCUMENTS 5,549,676 A * 8/1996 Johnson ............... A61F 2/08
                                                 623/13.13
5,639,278 A * 6/1997 Dereume ............. A61F 2/07
                                                 623/1.13
(Continued)

FOREIGN PATENT DOCUMENTS

| EP | 1842508 A1 | 10/2007 |
| WO | WO2014/072439 | 5/2014 |
| WO | WO 2015/173794 A1 | 11/2015 |

OTHER PUBLICATIONS

PCT communication dated Mar. 23, 2018 in corresponding PCT Appln.No. PCT/US2017/066199.

*Primary Examiner* — Kathleen S Holwerda
*Assistant Examiner* — Brigid K Byrd
(74) *Attorney, Agent, or Firm* — Medler Ferro Woodhouse & Mills PLLC

(57) ABSTRACT

A delivery system includes an elongated shaft component, a self-expanding valve prosthesis, at least one cinching suture, and a radially-expandable sleeve. The valve prosthesis is disposed over a distal portion of the elongated shaft component and includes a compressed configuration for delivery and an expanded configuration for deployment. The at least one cinching suture removably couples the valve prosthesis to the elongated shaft component and radially compresses the valve prosthesis into the compressed configuration for delivery. The sleeve is secured to and encircles an outer surface of the valve prosthesis. The sleeve has a delivery state with a first diameter extending over a full length of the valve prosthesis in the compressed configuration and a deployed state with a greater second diameter extending over the full length of the valve prosthesis in the expanded configuration. The sleeve is configured to prevent paravalvular leakage in situ in the deployed state.

17 Claims, 19 Drawing Sheets

(52) U.S. Cl.
CPC ............... *A61F 2210/0057* (2013.01); *A61F 2230/0069* (2013.01)

(58) Field of Classification Search
USPC .................. 623/1.15, 1.17, 1.2, 1.3, 2.11
See application file for complete search history.

(56) References Cited

U.S. PATENT DOCUMENTS

| | | | |
|---|---|---|---|
| 5,707,376 A * | 1/1998 | Kavteladze | A61F 2/90 623/1.11 |
| 5,843,167 A * | 12/1998 | Dwyer | A61F 2/07 623/1.14 |
| 5,984,926 A * | 11/1999 | Jones | A61B 17/686 606/309 |
| 6,077,297 A * | 6/2000 | Robinson | A61F 2/07 623/1.11 |
| 6,179,878 B1 * | 1/2001 | Duerig | A61F 2/07 128/898 |
| 6,203,572 B1 * | 3/2001 | Johnson | A61F 2/08 606/108 |
| 6,210,430 B1 * | 4/2001 | Solem | A61B 17/11 623/1.11 |
| 6,344,054 B1 * | 2/2002 | Parodi | A61F 2/962 623/1.13 |
| 6,352,561 B1 * | 3/2002 | Leopold | A61F 2/07 623/1.11 |
| 6,626,939 B1 * | 9/2003 | Burnside | A61F 2/07 623/1.38 |
| 6,676,692 B2 * | 1/2004 | Rabkin | A61F 2/95 604/104 |
| 6,702,845 B1 * | 3/2004 | Cully | A61F 2/95 29/282 |
| 7,044,966 B2 | 5/2006 | Svanidze et al. | |
| 7,276,078 B2 | 10/2007 | Spenser et al. | |
| 7,331,991 B2 | 2/2008 | Kheradvar et al. | |
| 7,510,572 B2 * | 3/2009 | Gabbay | A61F 2/2418 623/1.26 |
| 7,524,331 B2 | 4/2009 | Birdsall | |
| 7,534,261 B2 | 5/2009 | Friedman | |
| 7,628,805 B2 | 12/2009 | Spenser et al. | |
| 7,682,390 B2 * | 3/2010 | Seguin | A61B 17/072 623/1.26 |
| 7,708,775 B2 | 5/2010 | Rowe et al. | |
| 7,765,670 B2 * | 8/2010 | Spencer | A61F 2/95 29/451 |
| 7,780,725 B2 | 8/2010 | Haug et al. | |
| 7,914,487 B2 * | 3/2011 | Davies, Jr. | A61M 25/104 604/103 |
| 7,972,378 B2 | 7/2011 | Tabor et al. | |
| 8,142,497 B2 | 3/2012 | Friedman | |
| 8,182,528 B2 | 5/2012 | Salahieh et al. | |
| 8,231,670 B2 | 7/2012 | Salahieh et al. | |
| 8,449,599 B2 | 5/2013 | Chau et al. | |
| 8,603,160 B2 | 12/2013 | Salahieh et al. | |
| 8,623,078 B2 | 1/2014 | Salahieh et al. | |
| 8,641,757 B2 | 2/2014 | Pintor et al. | |
| 8,668,733 B2 | 3/2014 | Salahieh et al. | |
| 8,673,000 B2 | 3/2014 | Tabor et al. | |
| 8,734,484 B2 | 5/2014 | Ahlberg et al. | |
| 8,795,357 B2 * | 8/2014 | Yohanan | A61F 2/2418 623/2.14 |
| 8,801,706 B2 | 8/2014 | Rothstein et al. | |
| 8,801,776 B2 | 8/2014 | House et al. | |
| 8,808,356 B2 | 8/2014 | Braido et al. | |
| 8,852,272 B2 | 10/2014 | Gross et al. | |
| 8,926,690 B2 | 1/2015 | Kovalsky | |
| 8,986,371 B2 | 3/2015 | Quill et al. | |
| 8,986,375 B2 | 3/2015 | Garde et al. | |
| 8,992,608 B2 | 3/2015 | Haug et al. | |
| 9,226,839 B1 * | 1/2016 | Kariniemi | A61F 2/852 |
| 9,629,718 B2 * | 4/2017 | Gloss | A61F 2/24 |
| 9,763,819 B1 * | 9/2017 | Sondreaal | A61F 2/97 |
| 9,987,155 B1 * | 6/2018 | Sondreaal | A61F 2/962 |
| 2002/0002396 A1 * | 1/2002 | Fulkerson | A61F 2/95 623/1.11 |
| 2002/0032481 A1 * | 3/2002 | Gabbay | A61F 2/2418 623/2.11 |
| 2002/0038141 A1 * | 3/2002 | Yang | A61F 2/958 623/1.12 |
| 2002/0099436 A1 * | 7/2002 | Thornton | A61F 2/06 623/1.12 |
| 2002/0138129 A1 * | 9/2002 | Armstrong | A61F 2/07 623/1.11 |
| 2003/0060837 A1 * | 3/2003 | Solem | A61B 17/11 606/153 |
| 2003/0236565 A1 * | 12/2003 | DiMatteo | A61F 2/07 623/1.12 |
| 2005/0119722 A1 * | 6/2005 | Styrc | A61F 2/95 623/1.12 |
| 2005/0137690 A1 | 6/2005 | Salahieh | |
| 2005/0137697 A1 * | 6/2005 | Salahieh | A61F 2/2418 623/2.11 |
| 2005/0251243 A1 * | 11/2005 | Seppala | A61F 2/958 623/1.11 |
| 2007/0043425 A1 * | 2/2007 | Hartley | A61F 2/07 623/1.12 |
| 2007/0100427 A1 * | 5/2007 | Perouse | A61F 2/07 623/1.11 |
| 2007/0244544 A1 | 10/2007 | Birdsall et al. | |
| 2007/0270944 A1 | 11/2007 | Bergheim et al. | |
| 2008/0071343 A1 * | 3/2008 | Mayberry | A61F 2/954 623/1.11 |
| 2008/0195226 A1 * | 8/2008 | Williams | A61F 2/04 623/23.67 |
| 2008/0200979 A1 * | 8/2008 | Dieck | A61F 2/0077 623/1.44 |
| 2008/0275540 A1 | 11/2008 | Wen | |
| 2008/0319526 A1 * | 12/2008 | Hill | A61F 2/2418 623/1.12 |
| 2009/0030499 A1 * | 1/2009 | Bebb | A61F 2/07 623/1.13 |
| 2009/0099653 A1 | 4/2009 | Suri et al. | |
| 2009/0112311 A1 | 4/2009 | Miles et al. | |
| 2009/0192591 A1 | 7/2009 | Ryan et al. | |
| 2009/0306768 A1 * | 12/2009 | Quadri | A61F 2/2418 623/1.26 |
| 2010/0004740 A1 * | 1/2010 | Seguin | A61F 2/2412 623/2.18 |
| 2010/0036479 A1 | 2/2010 | Hill et al. | |
| 2010/0094394 A1 * | 4/2010 | Beach | A61F 2/91 623/1.11 |
| 2010/0168844 A1 | 7/2010 | Toomes et al. | |
| 2010/0185274 A1 * | 7/2010 | Moaddeb | A61F 2/2418 623/1.24 |
| 2010/0198238 A1 | 8/2010 | Sorajja | |
| 2010/0286768 A1 | 11/2010 | Alkhatib | |
| 2010/0298931 A1 * | 11/2010 | Quadri | A61F 2/2418 623/2.11 |
| 2010/0324651 A1 * | 12/2010 | Holzer | A61F 2/90 623/1.15 |
| 2011/0040366 A1 * | 2/2011 | Goetz | A61F 2/2418 623/1.12 |
| 2011/0257721 A1 | 10/2011 | Tabor | |
| 2011/0264206 A1 | 10/2011 | Tabor | |
| 2012/0022630 A1 * | 1/2012 | Wubbeling | A61F 2/95 623/1.11 |
| 2012/0078353 A1 * | 3/2012 | Quadri | A61F 2/2418 623/2.11 |
| 2012/0078360 A1 * | 3/2012 | Rafiee | A61F 2/2418 623/2.37 |
| 2012/0123529 A1 | 5/2012 | Levi et al. | |
| 2012/0130469 A1 * | 5/2012 | Cragg | A61F 2/07 623/1.11 |
| 2012/0130474 A1 * | 5/2012 | Buckley | A61F 2/97 623/1.12 |
| 2012/0209375 A1 * | 8/2012 | Madrid | A61F 2/2433 623/2.11 |
| 2012/0259401 A1 * | 10/2012 | Gerrans | A61F 2/958 623/1.11 |

(56) References Cited

U.S. PATENT DOCUMENTS

| | | | |
|---|---|---|---|
| 2012/0277734 A1 | 11/2012 | Goetz et al. | |
| 2013/0030519 A1 | 1/2013 | Tran | |
| 2013/0035749 A1* | 2/2013 | Farag | A61F 2/966 623/1.11 |
| 2013/0053941 A1* | 2/2013 | Costello | A61F 2/88 623/1.11 |
| 2013/0090714 A1* | 4/2013 | McHugo | A61F 2/90 623/1.11 |
| 2013/0096664 A1 | 4/2013 | Goetz et al. | |
| 2013/0096670 A1 | 4/2013 | Goetz et al. | |
| 2013/0103131 A1 | 4/2013 | Goetz et al. | |
| 2013/0190857 A1 | 7/2013 | Mitra et al. | |
| 2013/0190862 A1 | 7/2013 | Pintor et al. | |
| 2013/0197622 A1 | 8/2013 | Mitra et al. | |
| 2013/0204345 A1* | 8/2013 | Cully | A61F 2/966 623/1.12 |
| 2013/0218255 A1* | 8/2013 | Cattaneo | A61B 17/12118 623/1.11 |
| 2013/0245752 A1 | 9/2013 | Goetz et al. | |
| 2013/0245753 A1 | 9/2013 | Alkhatib | |
| 2013/0268000 A1* | 10/2013 | Hamer | A61F 2/0811 606/232 |
| 2013/0274873 A1 | 10/2013 | Delaloye et al. | |
| 2013/0325101 A1 | 12/2013 | Goetz et al. | |
| 2013/0331929 A1 | 12/2013 | Mitra et al. | |
| 2013/0338698 A1* | 12/2013 | Flanagan | A61M 25/104 606/194 |
| 2013/0338755 A1 | 12/2013 | Goetz et al. | |
| 2013/0338765 A1 | 12/2013 | Braido et al. | |
| 2014/0094904 A1 | 4/2014 | Salahieh et al. | |
| 2014/0107772 A1 | 4/2014 | Li et al. | |
| 2014/0114402 A1 | 4/2014 | Ahlberg et al. | |
| 2014/0114406 A1 | 4/2014 | Salahieh et al. | |
| 2014/0155990 A1* | 6/2014 | Nyuli | A61F 2/2418 623/2.11 |
| 2014/0194981 A1 | 7/2014 | Menk et al. | |
| 2014/0222144 A1 | 8/2014 | Eberhardt et al. | |
| 2014/0236287 A1* | 8/2014 | Clague | A61F 2/2418 623/2.11 |
| 2014/0243966 A1 | 8/2014 | Garde et al. | |
| 2014/0243969 A1 | 8/2014 | Venkatasubramanian et al. | |
| 2014/0257475 A1 | 9/2014 | Gross et al. | |
| 2014/0277388 A1 | 9/2014 | Skemp | |
| 2014/0277413 A1 | 9/2014 | Richter et al. | |
| 2014/0277417 A1 | 9/2014 | Schraut et al. | |
| 2014/0277422 A1 | 9/2014 | Ratz et al. | |
| 2014/0277423 A1 | 9/2014 | Alkhatib et al. | |
| 2014/0277424 A1 | 9/2014 | Oslund | |
| 2014/0277425 A1 | 9/2014 | Dakin | |
| 2014/0277426 A1 | 9/2014 | Dakin et al. | |
| 2014/0277428 A1 | 9/2014 | Skemp | |
| 2014/0296975 A1 | 10/2014 | Tegels et al. | |
| 2014/0316516 A1 | 10/2014 | Vidlund et al. | |
| 2014/0330368 A1* | 11/2014 | Gloss | A61F 2/24 623/2.11 |
| 2014/0343671 A1 | 11/2014 | Yohanan | |
| 2014/0350663 A1 | 11/2014 | Braido et al. | |
| 2014/0350665 A1 | 11/2014 | Braido et al. | |
| 2014/0350667 A1 | 11/2014 | Braido et al. | |
| 2014/0350668 A1 | 11/2014 | Delaloye et al. | |
| 2015/0005863 A1 | 1/2015 | Para | |
| 2015/0073538 A1* | 3/2015 | Thomas | A61F 2/2439 623/2.11 |
| 2015/0073540 A1 | 3/2015 | Salahieh et al. | |
| 2015/0073541 A1 | 3/2015 | Salahieh et al. | |
| 2015/0073544 A1 | 3/2015 | Gorman et al. | |
| 2015/0073548 A1 | 3/2015 | Matheny | |
| 2015/0112430 A1 | 4/2015 | Creaven et al. | |
| 2015/0122687 A1 | 5/2015 | Zeng et al. | |
| 2015/0127098 A1 | 5/2015 | Braido et al. | |
| 2015/0142100 A1 | 5/2015 | Morriss et al. | |
| 2015/0142103 A1 | 5/2015 | Vidlund | |
| 2015/0142104 A1 | 5/2015 | Braido | |
| 2015/0148898 A1 | 5/2015 | Krivoruchko et al. | |
| 2015/0157455 A1 | 6/2015 | Hoang et al. | |
| 2015/0216654 A1 | 8/2015 | Braido et al. | |
| 2015/0216663 A1 | 8/2015 | Braido et al. | |
| 2015/0250481 A1* | 9/2015 | Chobotov | A61B 17/12118 623/1.12 |
| 2015/0265442 A1* | 9/2015 | Styrc | A61F 2/2436 623/1.11 |
| 2015/0290007 A1* | 10/2015 | Aggerholm | A61F 2/958 623/1.11 |
| 2015/0313738 A1* | 11/2015 | Cully | A61B 17/00234 623/1.12 |
| 2015/0351943 A1* | 12/2015 | Shalev | A61F 2/07 623/1.12 |
| 2015/0374516 A1* | 12/2015 | Pereira | A61F 2/848 623/1.12 |
| 2016/0015543 A1* | 1/2016 | Perouse | A61F 2/844 623/1.12 |
| 2016/0184118 A1* | 6/2016 | Faber | A61F 2/95 623/1.11 |
| 2016/0250051 A1* | 9/2016 | Lim | A61F 2/2439 623/1.11 |
| 2016/0262880 A1* | 9/2016 | Li | A61F 2/2418 |
| 2017/0095331 A1* | 4/2017 | Spenser | A61F 2/2412 |
| 2017/0348101 A1* | 12/2017 | Vaughn | A61F 2/2436 |

\* cited by examiner

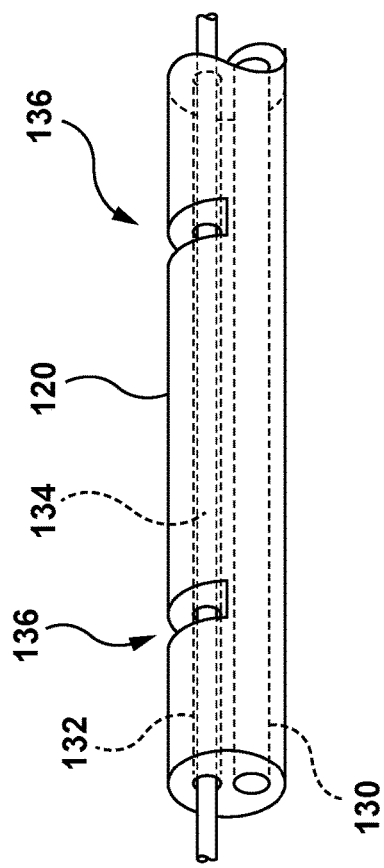
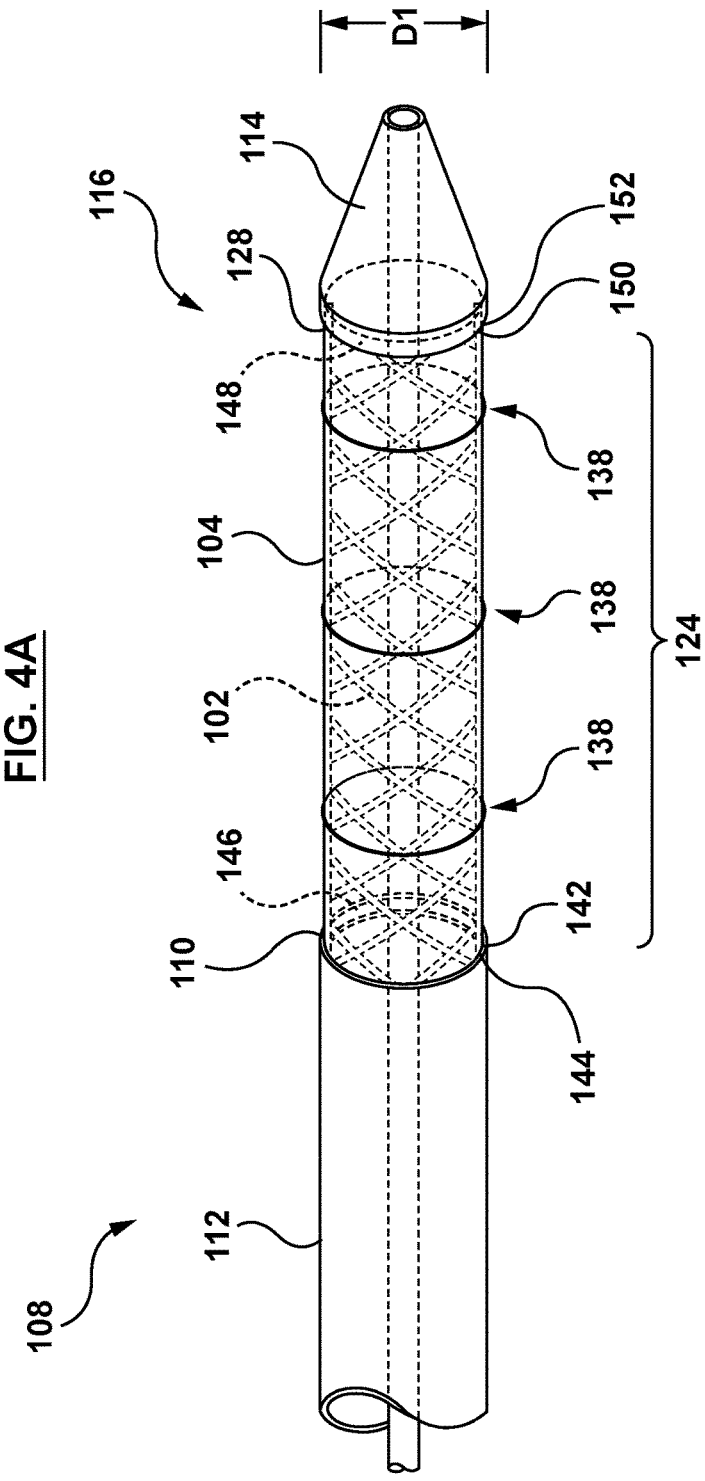
FIG. 4A
FIG. 4B

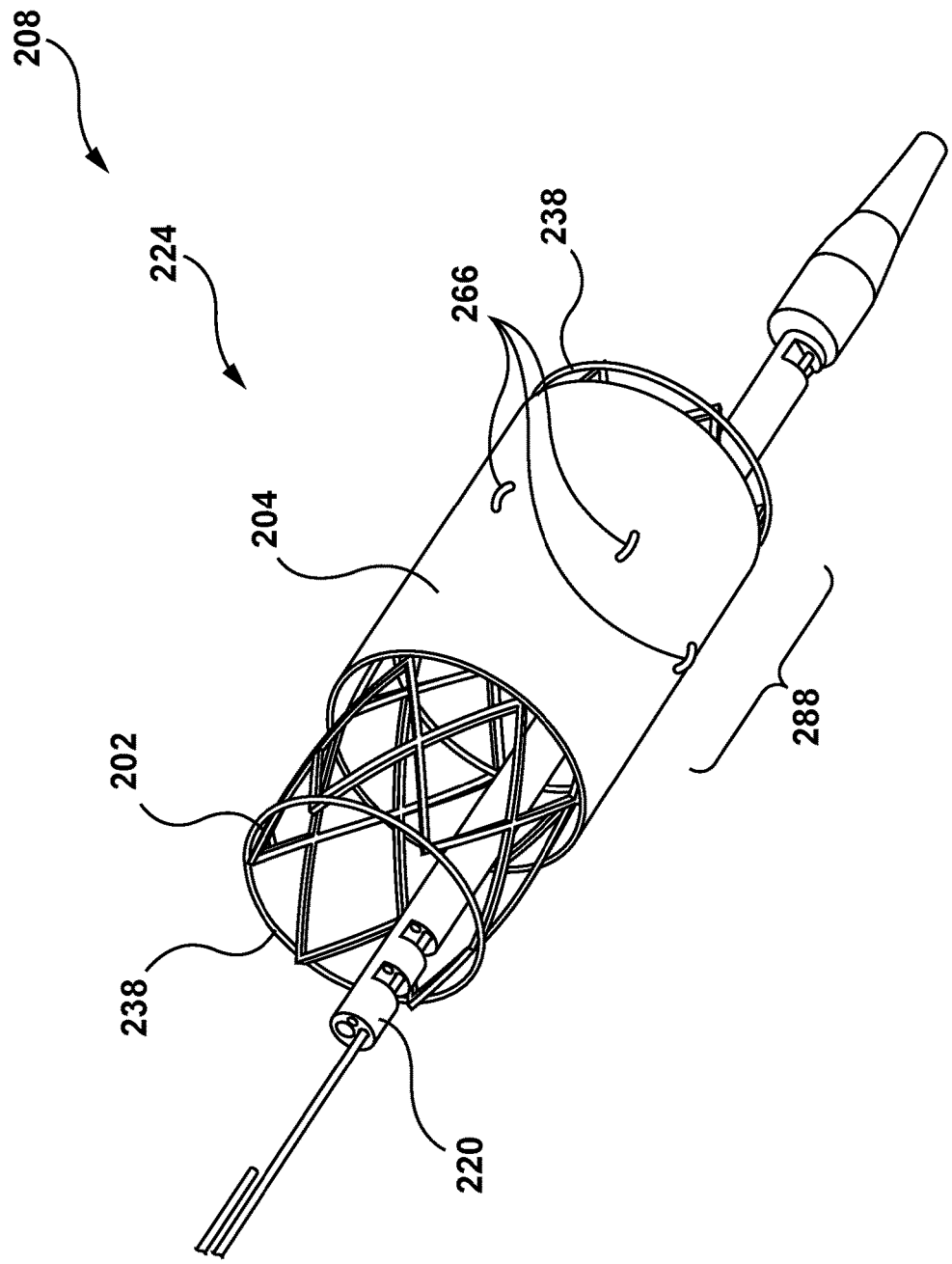

VALVE PROSTHESIS HAVING A RADIALLY-EXPANDABLE SLEEVE INTEGRATED THEREON FOR DELIVERY AND PREVENTION OF PARAVALVULAR LEAKAGE

FIELD OF THE INVENTION

The present technology relates generally to valve prostheses for intravascular delivery and associated systems and methods.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such valve prostheses can be percutaneously delivered and deployed at the site of the diseased heart valve through catheter-based systems. Such heart valve prostheses can be delivered while in a low-profile or compressed/contracted arrangement so that the valve prosthesis can be advanced through the patient's vasculature. Once positioned at the treatment site, the valve prosthesis can be expanded to engage tissue at the diseased heart valve region to, for instance, hold the valve prosthesis in position. While these valve prostheses offer minimally invasive methods for heart valve repair and/or replacement, challenges remain to providing effective, less invasive, smaller crossing profile prosthetic valve delivery systems, particularly for mitral valve replacement. For example, catheter delivery approaches and techniques for mitral valve replacement may utilized a transeptal approach. However, with the valve prosthesis retained within a capsule of the delivery system, challenges, such as capsule travel within the confined space of the left atrium may limit positioning of a heart valve prosthesis in the native mitral valve. Moreover, the capsule adds to the crossing profile of the catheter. Catheter crossing profile, especially for inter-atrial septum puncture, limit both the feasibility of heart valve prosthetic delivery as well as the size of the heart valve prosthesis. Alternatively, elimination of the capsule and radial contraction of the valve prosthesis by methods such as cinching reduces crossing profile of the catheter, but the exposed or uncovered valve prosthesis may damage native anatomy during delivery.

Further, in some patients, the valve prosthesis may not perform as desired following implantation. For example, the valve prosthesis may not 100% coapt to the wall of the native valve, resulting in paravalvular leakage (PVL). A sealing element or skirt may be disposed between the wall of the native valve and the valve prosthesis to limit PVL. However, inclusion of a sealing sleeve also adds to the crossing profile of the catheter.

Accordingly, there is a need for a system that minimizes the crossing profile of a catheter, provides sealing of a valve prosthesis to a native valve wall, and assists in atraumatic delivery of the valve prosthesis to the target site.

BRIEF SUMMARY OF THE INVENTION

Embodiment hereof are directed to a delivery system for percutaneously delivering a self-expanding valve prosthesis including an elongated shaft component, the valve prosthesis, at least one cinching suture, and a radially-expandable sleeve. The valve prosthesis is disposed over a distal portion of the elongated shaft component. The valve prosthesis has a compressed configuration for delivery within a vasculature and an expanded configuration for deployment. The at least one cinching suture is configured for coupling the valve prosthesis to the elongated shaft component. The at least one cinching suture is removable and radially compresses the valve prosthesis into the compressed configuration for delivery. The radially-expandable sleeve is secured to and encircles an outer surface of the valve prosthesis. The radially-expandable sleeve is configured to transform from a delivery state in which the radially-expandable sleeve has a first diameter and extends over a full length of the valve prosthesis in the compressed configuration to a deployed state in which the radially-expandable sleeve has a second diameter greater than the first diameter and extends over the full length of the valve prosthesis in the expanded configuration. The radially-expandable sleeve is configured to prevent paravalvular leakage in situ in the deployed state.

Embodiments hereof are also directed to a delivery system for percutaneously delivering a self-expanding valve prosthesis including an elongated shaft component, the valve prosthesis, at least one cinching suture, and a radially-expanding sleeve. The valve prosthesis is disposed over a distal portion of the elongated shaft component. The valve prosthesis has a compressed configuration for delivery within a vasculature and an expanded configuration for deployment. The at least one cinching suture is configured for coupling the valve prosthesis to the elongated shaft component. The at least one cinching suture is removable and radially compresses the valve prosthesis into the compressed configuration for delivery. The radially-expandable sleeve is secured to and encircles an outer surface of the valve prosthesis. The radially-expandable sleeve is configured to transform from a delivery state in which the radially-expandable sleeve has a first diameter and extends over a full length of the valve prosthesis in the compressed configuration to a deployed state in which the radially-expandable sleeve has a second diameter greater than the first diameter and extends over a portion of the valve prosthesis in the expanded configuration. The radially-expandable sleeve is configured to prevent paravalvular leakage in situ in the deployed state.

Embodiments hereof are further directed to a delivery system for percutaneously delivering a self-expanding valve prosthesis including an elongated shaft component, the valve prosthesis, at least one cinching suture, and a radially-expandable sleeve. The valve prosthesis is disposed over a distal portion of the elongated shaft component. The valve prosthesis has a compressed configuration for delivery within a vasculature and an expanded configuration for deployment. The at least one cinching suture is configured for coupling the valve prosthesis to the elongated shaft component. The at least one cinching suture is removable and radially compresses the valve prosthesis into the compressed configuration for delivery. The radially-expandable sleeve is secured to and encircles an outer surface of the valve prosthesis. The radially-expandable sleeve is configured to transform from a delivery state in which the radially-expandable sleeve has a first diameter and extends over a full length of the valve prosthesis in the compressed configuration and forms an outermost component of the delivery system for a longitudinal portion thereof to a deployed state in which the radially-expandable sleeve has a second diameter greater than the first diameter and extends over at least a portion of the valve prosthesis in the expanded configuration. The radially-expandable sleeve is configured to prevent paravalvular leakage in situ in the deployed state.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIG. 4A is a partial perspective cross-sectional illustration of a distal portion of an elongated shaft component of the delivery system of FIG. 3 in accordance with an embodiment hereof.

FIG. 4B is a partial perspective illustration of the distal portion of the delivery system of FIG. 3, with a valve prosthesis in the compressed configuration, in accordance with an embodiment hereof.

FIG. 9B is a perspective illustration of the distal portion of the delivery system of FIG. 9A with the valve prosthesis in transformation from the compressed configuration to the expanded configuration.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a catheter, catheter assembly, or delivery catheter. For example, "distal" or "distally" are a position distant from or in a direction away from the clinician when referring to delivery procedures or along a vasculature. Likewise, "proximal" and "proximally" are a position near or in a direction toward the clinician.

The following detailed description is merely exemplary in nature and is not intended to limit the present technology or the application and uses of the present technology. Although the description of embodiments hereof is in the context of treatment of heart valves and particularly in the context of gaining percutaneous access to a mitral or aortic valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat or access one or more of many valves of the body including valves of the heart such as the mitral and aortic valves. The embodiments of the present technology can be therapeutically combined with many known surgeries and procedures, for example, such embodiments can be combined with known methods of intravascularly accessing the valves of the heart such as the aortic valve and mitral valve with retrograde approaches and combinations of retrograde and antegrade approaches.

Figure 1:
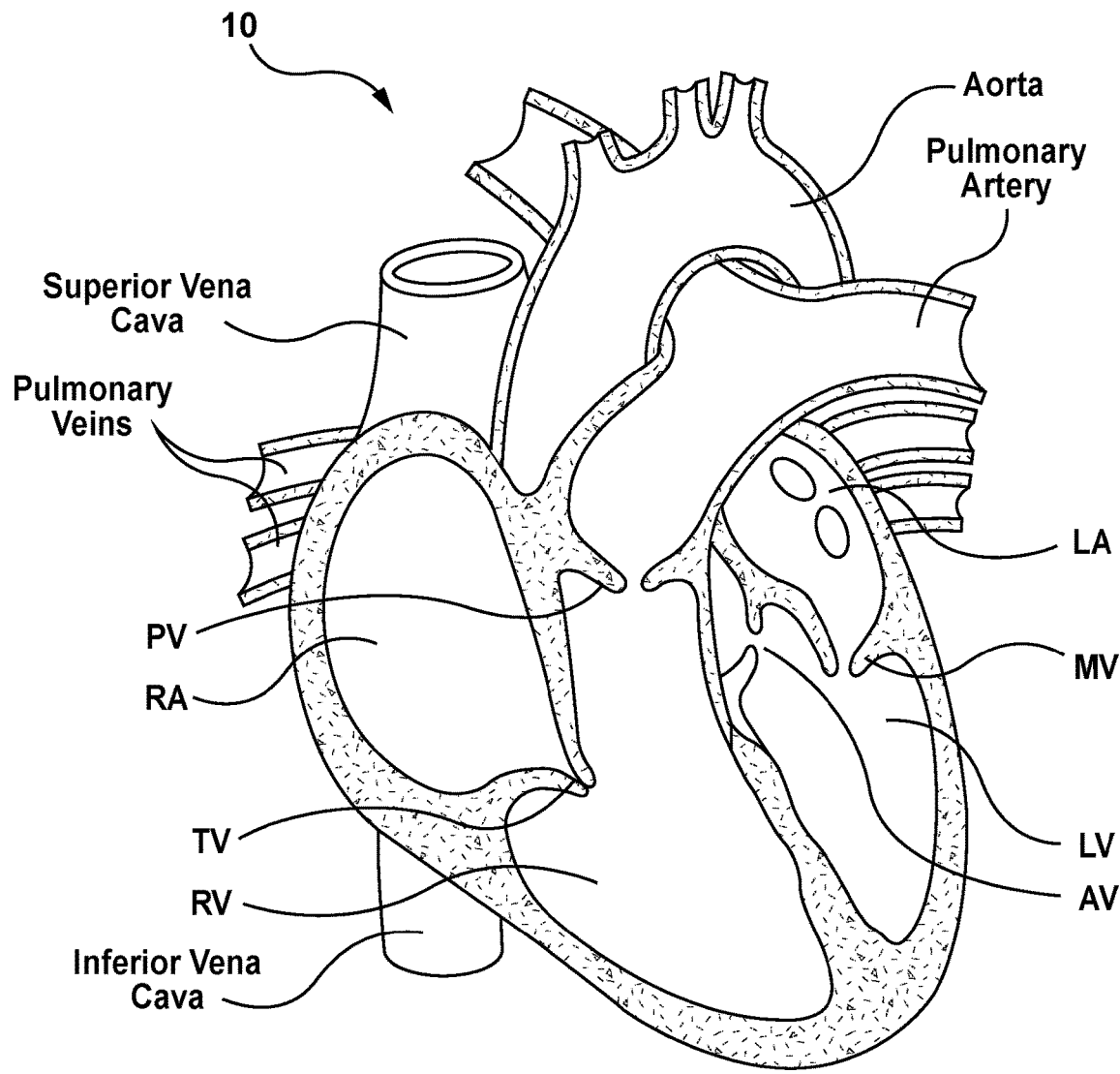
FIG. 1 is a schematic sectional illustration of a mammalian heart having native valve structures.
Figure 2B:
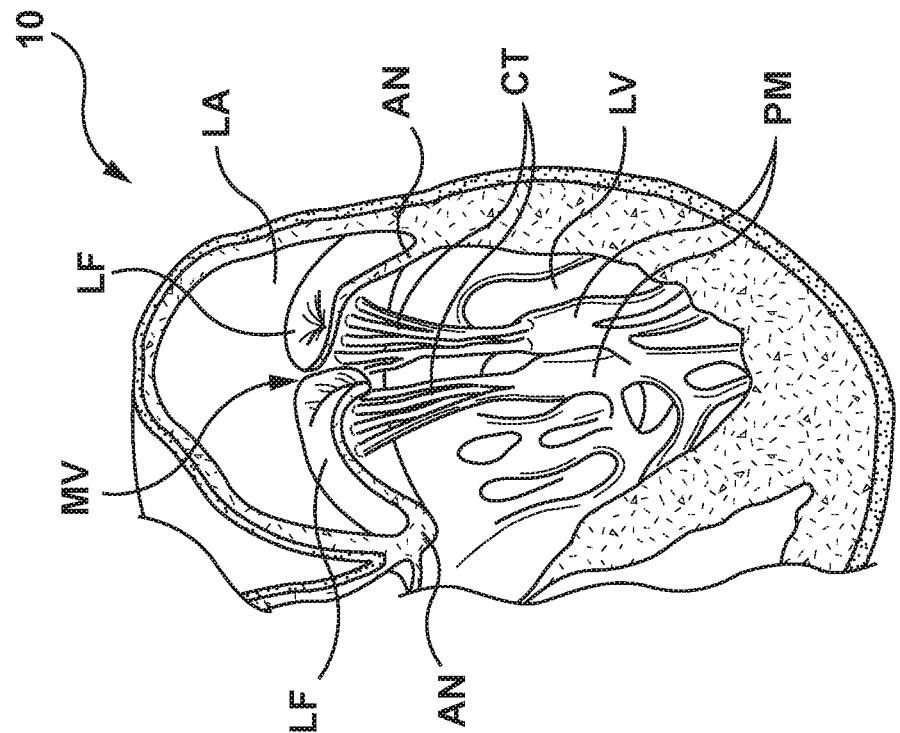
FIG. 2B is a schematic sectional illustration of the left ventricle of a heart having a prolapsed mitral valve in which the leaflets do not sufficiently co-apt and which is suitable for replacement with a valve prosthesis via a delivery system in accordance with embodiments hereof.
Figure 2A:
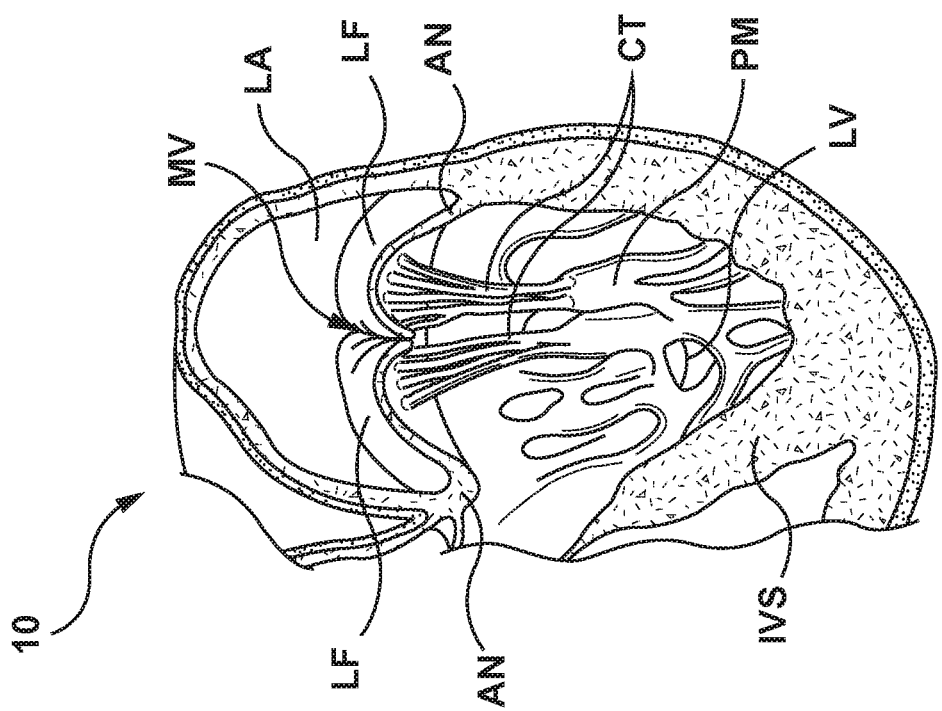
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, as shown in FIG. 2A, the leaflets LF of the native mitral valve MV meet evenly at the free edges or "coapt" to close and prevent back flow of blood into left atria LA during contraction of the left ventricle LV. The tissue of the leaflets LF attach the surrounding heart structure via a dense fibrous ring of connective tissue called an annulus AN which is distinct from both the tissue of the leaflets LF as well as the adjoining muscular tissue of the heart wall. In general, the connective tissue at the annulus AN is more fibrous, tougher and stronger than leaflet tissue. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Embodiments of delivery systems, delivery catheters, and associated methods in accordance with the present technology are described in this section with reference to FIGS. 3-10C. It will be appreciated that specific elements, substructures, uses, advantages, and/or other aspects of the embodiments described herein and with reference to FIGS. 3-10C can be suitably interchanged, substituted or otherwise configured with one another in accordance with additional embodiments of the present technology.

Provided herein are systems, assemblies, catheters, devices and methods suitable for intravascular delivery of a heart valve prosthesis to a native valve in a heart of a patient. In some embodiments, delivery catheters and methods are presented for the treatment of valve disease as part of procedure steps for minimally invasive implantation of an artificial or prosthetic heart valve, such as a mitral valve. For example, a heart valve delivery system, in accordance with embodiments described herein, can be used to percutaneously direct and deliver a mitral valve prosthesis via an intravascular retrograde approach across an aortic valve, into a left ventricle and across a diseased or damaged mitral valve in a patient, such as in a patient suffering from mitral valve prolapse illustrated in FIG. 2B. In another embodiment, a heart valve delivery system, in accordance with embodiments described herein, can be used to direct and deliver an aortic valve prosthesis via an aortic approach across an aortic arch, into an aortic sinus and across a diseased or damaged aortic valve in a patient. In further embodiments, the delivery systems and delivery catheters disclosed herein are suitable for prosthetic heart valve delivery across other diseased or damaged natural heart valves or prior implanted prosthetic heart valves, such as tricuspid, and pulmonary heart valves.

Figure 3:
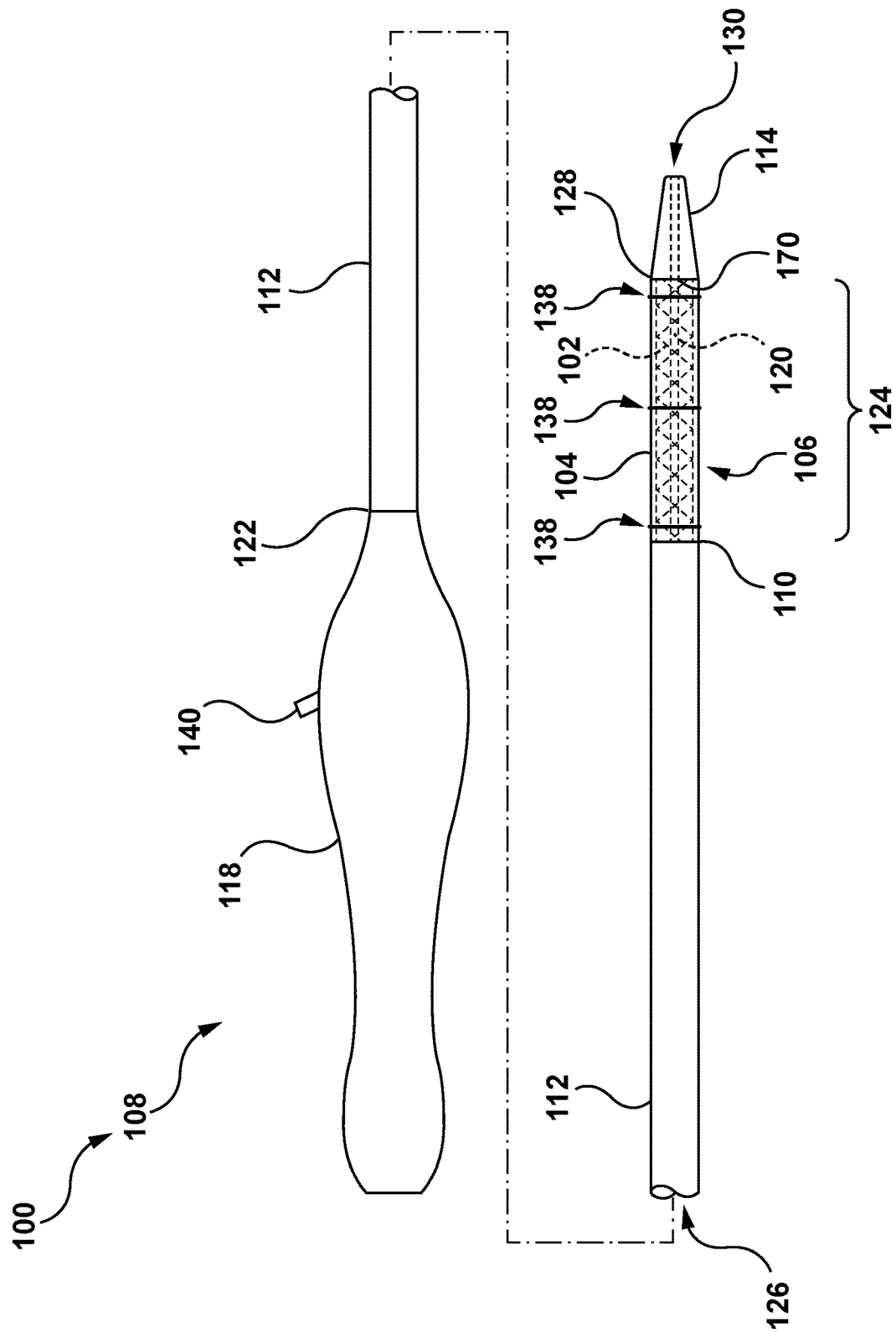
FIG. 3 is a side illustration of a minimally invasive heart valve prosthesis delivery system configured in accordance with an embodiment hereof.

FIG. 3 is a side view of a minimally invasive heart valve prosthesis delivery system 100 (hereinafter referred to as "delivery system 100" for sake of simplicity) configured in accordance with an embodiment hereof, wherein a compressed self-expanding valve prosthesis 102 (hereinafter referred to as "valve prosthesis 102" for sake of simplicity) and a radially-expandable sleeve 104 (hereafter referred to as "sleeve 104" for sake of simplicity) are visible extending within a portion 106 of a delivery catheter 108, between a distal end 110 of an outer shaft 112 and a distal tip 114 of the delivery catheter 108. In an embodiment, the valve prosthesis 102 includes a tubular stent or frame and a prosthetic component disposed within and secured to the stent. The valve prosthesis 102 is held in its compressed configuration for delivery by a cinching assembly 116, which includes one or more loops of a suture(s) or cord (s), as described in more detail with reference to FIGS. 4A and 4B below. Due to the cinching assembly 116, the delivery catheter 108 beneficially does not include or require a retractable capsule for compressing the valve prosthesis 102 and thus eliminates the need to retract or advance a retractable capsule relative to the valve prosthesis 102 during delivery, and therefore may be more efficiently utilized within the confines of native anatomy having small or restricted space such as but not limited to the left atria. However, the delivery catheter 108 includes the sleeve 104 coupled to and covering the compressed valve prosthesis 102. The sleeve 104 in a delivery state offers an atraumatic outer surface (in comparison to an uncovered or exposed outer surface of the valve prosthesis 102) covering or extending the length of the valve prosthesis 102 in the compressed configuration to reduce potential damage to vasculature tissue during delivery. Even further, the sleeve 104 is configured to remain with the valve prosthesis 102 when deployed and to transform or convert to a deployed state upon deployment to provide sealing of the valve prosthesis 102 to the wall of the native valve region so as to prevent paravalvular leakage (PVL), as described in greater detail below. Thus, the sleeve 104 combines the functionality of a capsule during tracking or delivery and a skirt for prevention of PVL after deployment while minimizing the crossing profile of the delivery catheter 108, particularly in a distal segment 124 thereof, during delivery.

As shown in FIG. 3, the delivery system 100 includes the delivery catheter 108 having a handle component 118 operatively coupled to a remainder thereof as described herein. In an embodiment, the delivery catheter 108 includes the handle component 118, the outer shaft 112, an elongated shaft component 120 (may also be referred to as an inner shaft), portions of the cinching assembly 116 (not shown in FIG. 3), and the distal tip 114. The delivery system 100 is sized and configured to be advanced through the vasculature in a minimally invasive manner. An introducer sheath (not shown) or outer sheath (not shown) may be used with the delivery catheter 108 to minimize intravascular trauma during introduction, tracking and delivery of the delivery catheter 108 to a target location.

Referring to FIG. 3, the outer shaft 112 is a generally hollow body, extending from at least a distal end 122 of the handle component 118 to the distal segment 124 of the delivery catheter 108. The outer shaft 112 defines a lumen 126 there through configured to receive the elongated shaft component 120 therein. In an embodiment, the outer shaft 112 of the delivery catheter 108 is operably coupled to the handle 118 and is slidable or translatable relative to the elongated shaft component 120.

The elongated shaft component 120 is a generally hollow body defining a plurality of lumens there through. The elongated shaft component 120 extends from at least the distal end 122 of the handle 118 to at least a proximal end 128 of the distal tip 114. In an embodiment, the elongated shaft component 120 includes a guidewire lumen 130 and a cinch lumen 132, as shown in FIG. 4A. In other embodiments, the elongated shaft component 120 may include more or fewer lumen based upon the application. The guidewire lumen 130 is configured to slidably receive a guidewire (not shown) therein. The cinch lumen 132 is configured to slidably receive a cinch release pin 134 therein, as described in greater detail below. The elongated shaft component 120 further includes a plurality of cinch notches 136. Each cinch notch 136 is an opening in the outer wall of the elongated shaft component 120 extending from an outer surface to an inner surface, there through for access to the cinch lumen 132.

The delivery catheter 108 terminates with the distal tip 114. The distal tip 114 is configured to facilitate introduction and movement of the distal segment 124 within the target heart chamber and towards the target valve region in a manner that prevents or reduces trauma to the surrounding heart tissue structures (e.g., chordae tendinae, papillary muscles, leaflets, annulus, etc.). The distal tip 114 may be a flexible curved or tapered tip. The curvature of the distal tip 114 can be varied depending upon the particular sizing or configuration of the sleeve 104 and/or the valve prosthesis 102. In some embodiments, the distal tip 114 may also comprise one or more radiopaque markers (not shown) and/or one or more sensors (not shown) for facilitating positioning and placement of the valve prosthesis 102 by the clinician or operator. In an embodiment, the distal tip 114 may be coupled to a distal end 170 of the elongated shaft component 120. In an embodiment, the distal tip 114 may include a distal portion of the guidewire lumen 130 aligned with the guidewire lumen 130 of the elongated shaft component 120 for facilitating an over-the-wire ("OTW") delivery of the delivery catheter 108 to a target location. In other embodiments, a delivery catheter in accordance herewith may be adapted to have a guidewire lumen along only a distal segment thereof so as to be suitable for use with rapid-exchange ("RX") techniques. The distal tip 114 may be made from a polymer material (e.g., a polyether block amide copolymer sold under the trademark PEBAX, or a thermoplastic polyether urethane material sold under the trademarks ELASTHANE or PELLETHANE), or other suitable materials having the desired properties, including a selected durometer. In other embodiments, the distal tip 114 may be formed from different material(s) and/or have a different arrangement.

Figure 4C:
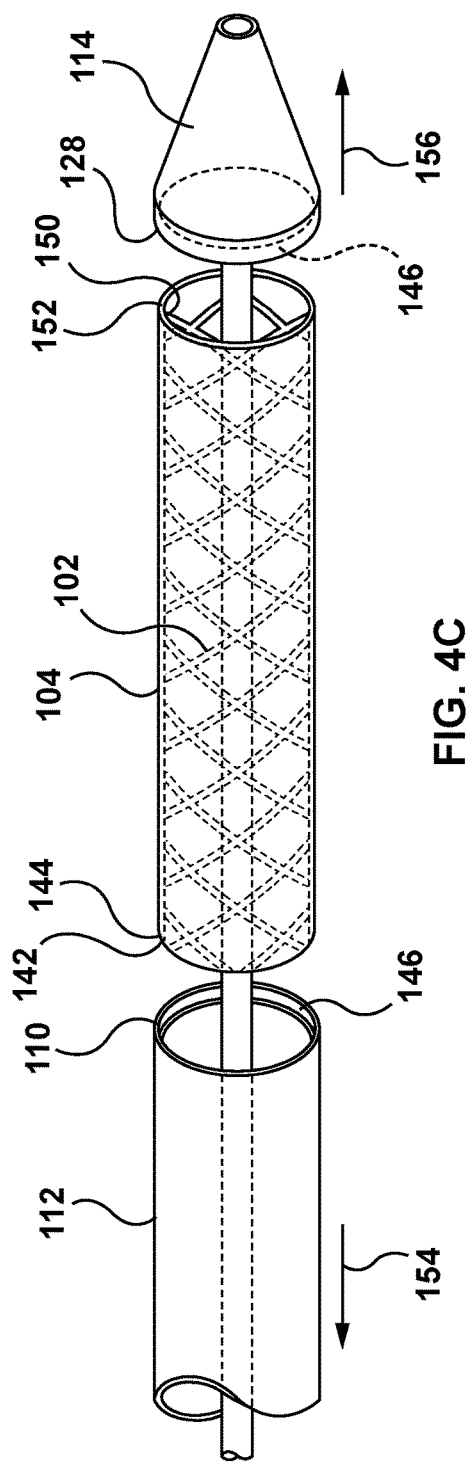
FIG. 4C is another partial side illustration of the distal portion of the delivery system of FIG. 4B.

In the delivery configuration, the delivery catheter 108 is configured to be introduced within a patient's vasculature to position the valve prosthesis 102 at a target location such as a heart chamber (e.g., left atria) adjacent a damaged or diseased heart valve (e.g., mitral valve). FIG. 4B is an enlarged partial perspective side view of the distal segment 124 of the delivery catheter 108 in the delivery configuration with the valve prosthesis 102 is the compressed configuration and the sleeve 104 in a delivery state in accordance with an embodiment hereof. Upon advancement/delivery to the target location, the delivery catheter 108 is transformable to a deployed configuration with the valve prosthesis 102 in the expanded configuration and the sleeve 104 in the deployed state, aligned and positioned within the damaged or diseased heart valve for repair or valve replacement. FIG. 4C is an enlarged partial perspective side view of the delivery catheter 108 in the deployed configuration with the valve prosthesis 102 in the expanded configuration and the sleeve 104 in the deployed state with the sleeve 104 covering the full length of the valve prosthesis 102.

Referring to FIG. 4B, when the delivery catheter 108 is in the delivery configuration, the valve prosthesis 102 is retained by the cinching assembly 116. The cinching assembly 116 includes the cinch release pin 134 and at least one cinching suture 138 coupled thereto. The cinching assembly 116 is configured to compressively constrain the valve prosthesis 102 in the compressed configuration for delivery to a native heart valve and to controllably release the compressive constrain such that the valve prosthesis 102 may controllably expand to the expanded configuration at the desired treatment site. The cinching suture(s) 138 are disposed about at least a portion of the self-expanding valve prosthesis 102 such that pulling the cinching suture 138 controls constriction/compression of the valve prosthesis 102 and releasing/removing the one or more cinching sutures 138 controls expansion/deployment of the valve prosthesis 102. Examples of suitable cinch assemblies for retaining self-expanding valve prostheses are described in U.S. Patent Publication No. 2014/0330368 to Gloss, which is incorporated herein by reference in its entirety. In an embodiment, the cinching assembly 116 includes three (3) cinching sutures or suture loops 138, as shown in FIG. 4B. Each cinching suture 138 encircles or extends circumferentially around an outer surface of the sleeve 104 and the valve prosthesis 102 disposed therein, such that the cinching sutures 138 constrain the valve prosthesis 102 in the compressed configuration, releasably coupling the valve prosthesis 102 and the sleeve 104 to the elongated shaft component 120, as shown in FIG. 4B. Alternatively, each cinching suture 138 may extend circumferentially around only the outer surface of the valve prosthesis 102 and within an inner surface of the sleeve 104. Each cinching suture 138 further extends through the respective cinch notch 136 and couples with the cinch release pin 134 disposed within the cinch lumen 132 of the elongated shaft component 120. The cinch release pin 134 is operably coupled to the handle 118 at a proximal end (not shown) and is slidable or translatable relative to the elongated shaft component 120. Cinching assembly 116 is configured such that remote actuation of the cinch release pin 134 (e.g., via an actuator 140 shown on FIG. 3, such as a knob, pin, or lever carried by the handle component 118) with the valve prosthesis 102 in the compressed configuration controllably releases the cinching sutures 138 such that the valve prosthesis 102 radially expands to the expanded configuration.

In an embodiment, when the valve prosthesis 102 is retained by the cinching assembly 116 into the compressed configuration, a first end 142 of the valve prosthesis 102 and/or a first end 144 of the sleeve 104 are retained within a circumferential recess 146 on an inner surface of the distal end 110 of the outer shaft 112, as shown in FIG. 4B. Further, in the delivery configuration, a second end 150 of the valve prosthesis 102 and/or a second end 152 of the sleeve 104 are retained within a circumferential recess 148 on an inner surface of the proximal end 128 of the distal tip 114. In the delivery configuration, the delivery catheter 108 is configured to carry the valve prosthesis 102 and the sleeve 104 in a low-profile (compressed configuration and delivery state, respectively) for delivery through the vasculature.

Figure 4D:
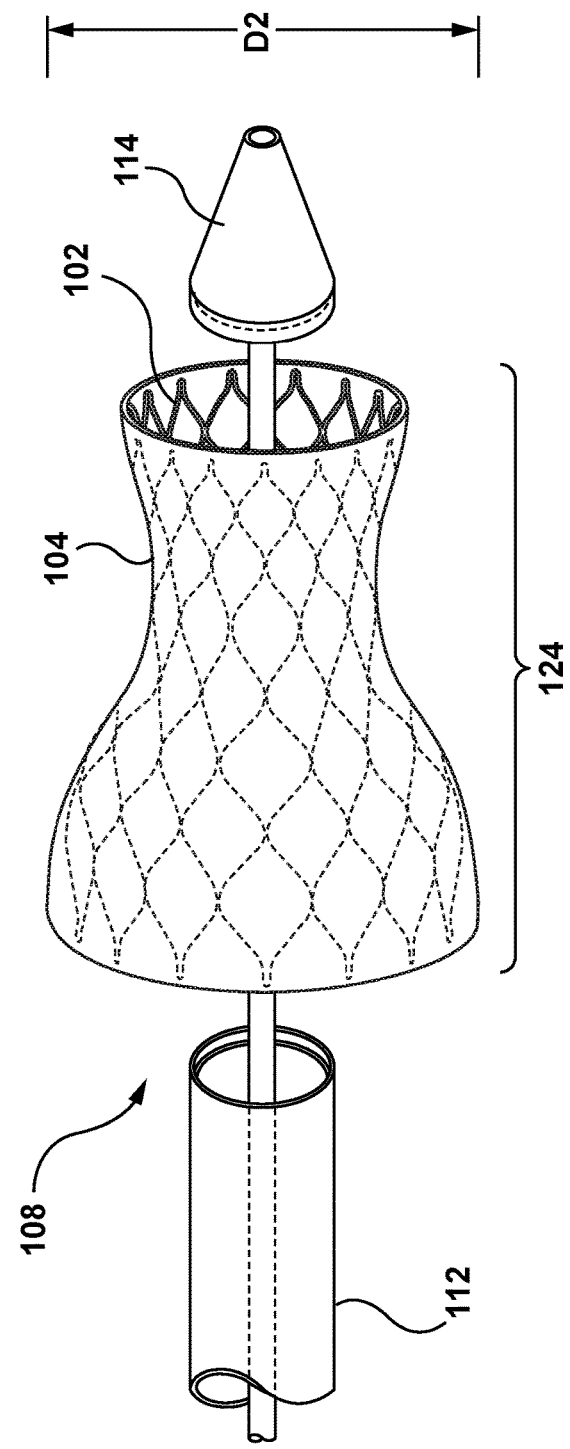
FIG. 4D is a partial perspective illustration of the distal portion of the delivery system of FIG. 3 with the valve prosthesis in the expanded configuration, in accordance with an embodiment hereof.

Referring to FIGS. 4C and 4D, when the delivery catheter 108 is in the deployed configuration, the valve prosthesis 102 is controllably released to radially expand to the expanded configuration by actuation of the cinching assembly 116 and release of the cinching sutures 138 as described above with respect to FIGS. 4A and 4B. In an embodiment, the outer shaft 112 is retracted in a proximal direction (arrow 154) and the distal tip 114 is advanced in a distal direction (arrow 156) at or prior to actuation of the cinching assembly 116 such that the first end 142 of the valve prosthesis 102 and/or the first end 144 of the sleeve 104 are no longer retained within the circumferential recess 146 of the distal end 110 of the outer shaft 112 and the second end 150 of the valve prosthesis 102 and/or the second end 152 of the sleeve 104 are no longer retained within the circumferential recess 148 at the proximal end 128 of the distal tip 114, respectively, as shown in FIG. 4C. Radial expansion of the valve prosthesis 102 presents an outward radial force on an inner surface of the sleeve 104 such that the sleeve 104 expands to the deployed state, as shown in FIG. 4D.

Accordingly, the sleeve 104 is radially expandable from the delivery state to the deployed state with outward radial force applied thereto. The sleeve 104 has a first diameter D1 (shown in FIG. 4B) when in the delivery state and a second diameter D2 (shown in FIG. 4D) when in the deployed state, wherein the first diameter D1 is less than the second diameter D2. The sleeve 104 is therefore coupled only to the valve prosthesis 102 and is not directly coupled to the delivery catheter 108. In this embodiment, the sleeve 104 covers the full length of the valve prosthesis 102 when in both the delivery state and the deployed state. The sleeve 104 is configured to cover the length of the valve prosthesis 102 in the compressed configuration such that the outer surface of the sleeve 104 (with the valve prosthesis 102 disposed therein) presents a generally smooth outer surface such that the valve prosthesis 102 may be advanced through the vasculature of a patient without damage to the surrounding tissue. The sleeve 104 is further configured to radially expand to the deployed state by an outward radial force applied thereto (e.g. upon transformation of the valve prosthesis 102 to the expanded configuration) such that the sleeve 104 is disposed or embedded between the full length of the valve prosthesis 102 and the wall of the native valve. When so embedded, the sleeve 104 provides sealing of the valve prosthesis 102 to the wall of the native valve, thus preventing paravalvular leakage (PVL). Stated another way, the sleeve 104 is configured to or functions as a cover that prevents damage to the vasculature as the valve prosthesis 102 is advanced through a patient, and is further configured to or functions as a sealing component after the valve prosthesis 102 is radially expanded to the expanded configuration within the annulus of a target valve. The sleeve 104 may further include a biologically or pharmacologically active substance for example, and not by way of limitation, an anti-calcification substance, or other substances or combinations of substances suitable for the purposes described herein.

Figure 5B:
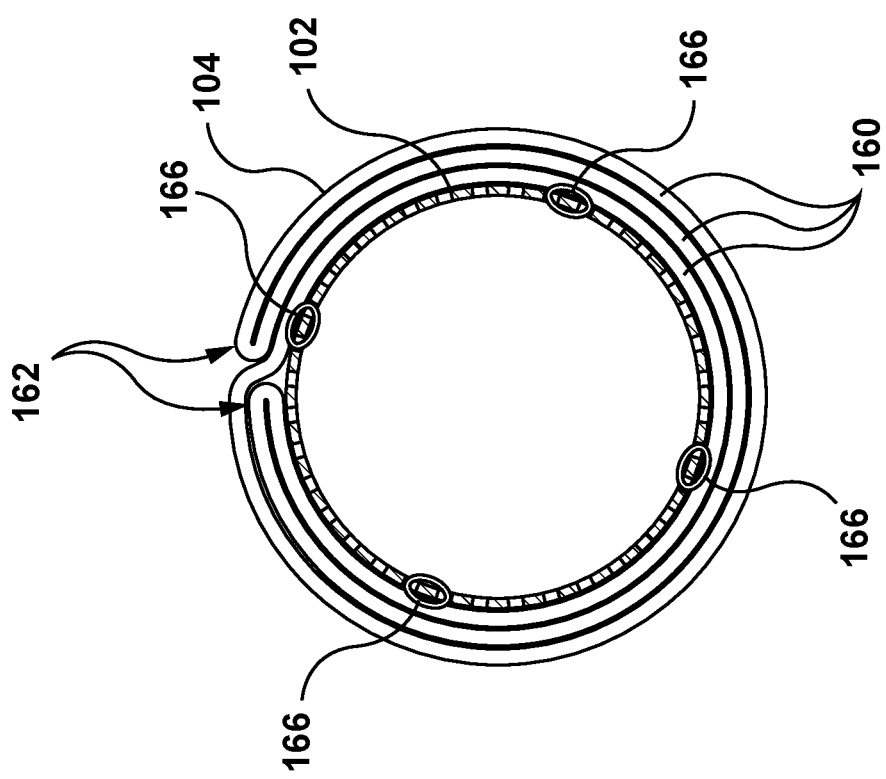
FIG. 5B is a cross-sectional illustration of the sleeve taken at line 5B-5B of FIG. 5A.
Figure 5A:
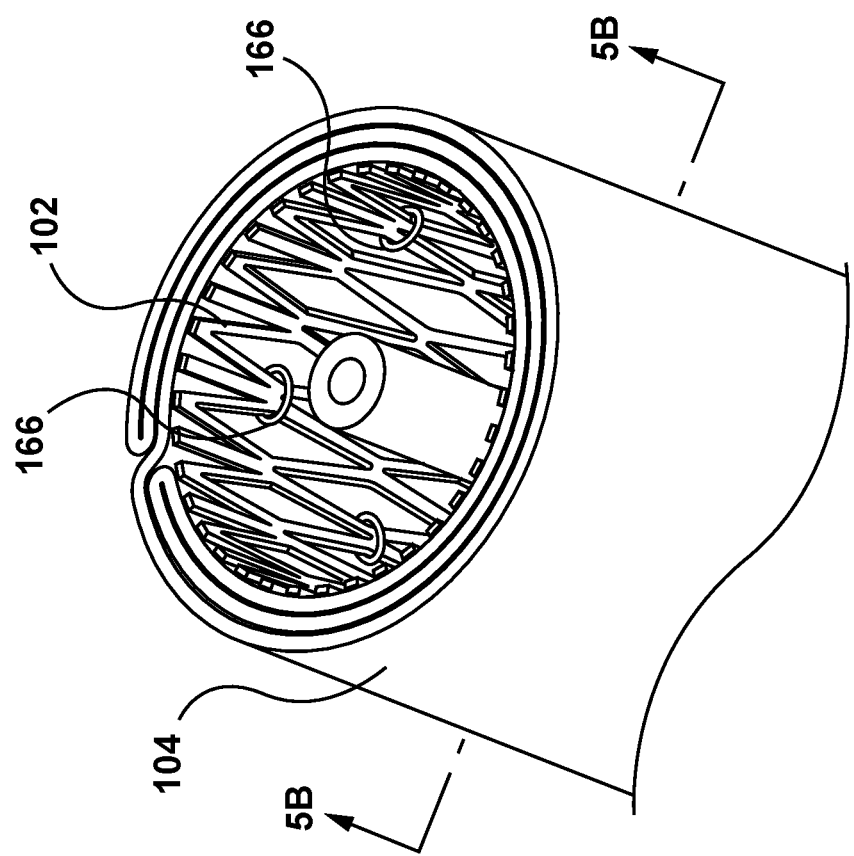
FIG. 5A is a partial perspective illustration of a sleeve of the delivery device of FIG. 3 in accordance with an embodiment hereof.
Figure 5C:
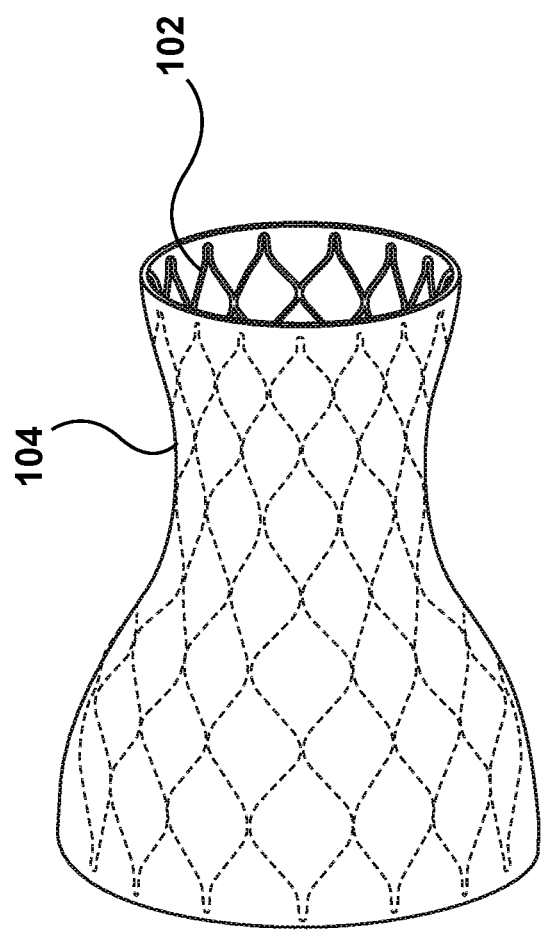
FIG. 5C is a perspective illustration of the sleeve of FIG. 5A in the deployed state.

In an embodiment, in order for the sleeve 104 to be radially expandable from the delivery state to the deployed state, the sleeve 104 is a folded material wrapped about an outer surface of the valve prosthesis 102 in the compressed configuration, as shown in FIG. 5A and FIG. 5B and in the expanded configuration in FIG. 5C. More specifically, the sleeve 104 includes a smooth outer surface and is comprised of a plurality of concentric layers 160 wrapped about the outer surface of the valve prosthesis 102 in a series of folds 162. While the example of FIGS. 5A-5B show the sleeve 104 with two (2) folds 162 this is not meant to limit the design and other configurations are contemplated. As the valve prosthesis 102 transforms from the compressed configuration to the expanded configuration, the sleeve 104 disposed thereon is configured to unfold as the sleeve 104 transforms form the delivery state to the deployed state. FIG. 5C shows the smooth outer surface of the sleeve 104 in the deployed state over the valve prosthesis 102 in the expanded configuration. In an embodiment, the sleeve 104 is coupled to the valve prosthesis 102 by at least one sleeve-anchoring suture 166 such that the sleeve 104 will not slide or translate or migrate or otherwise undesirably move relative to the valve prosthesis 102 during delivery and deployment (due to the slippery nature of the sleeve 104). More specifically, the sleeve 104 is coupled to the valve prosthesis 102 such that the sleeve 104 maintains proper position over the outer surface of the valve prosthesis 102 when in either the delivery or the deployed state. Thus, the sleeve 104 is integrated onto the valve prosthesis 102. In an embodiment, the sleeve 104 is coupled to the valve prosthesis 102, for example, in four (4) axial segments (90°) by four (4) sleeve-anchoring sutures 166. In other embodiments, the sleeve 104 may be coupled to the valve prosthesis 102 by more or fewer axial segment and more or fewer sleeve-anchoring sutures 166. In still other embodiments, the sleeve 104 may be coupled to the valve prosthesis 102 by other methods such as, but not limited to bonding, adhesives, or other methods suitable for the purposes disclosed herein. The sleeve 104 is a structure that allows the sleeve 104 to stretch or expand to the deployed state when the valve prosthesis 102 in the expanded configuration is disposed therein. In an embodiment, the sleeve 104 is of an elastic material. In an alternative embodiment, the sleeve 104 may be of a shape memory material with a pre-set shape in the folded/wrapped delivery state. A desired radial stiffness of the sleeve 104 may be provided using variations in the structure and/or density of the shape memory material. The shape memory sleeve 104 is configured to return to the delivery state when not acted upon by an outside force (e.g. the valve prosthesis 102 in the expanded configuration, disposed therein). The sleeve 104 may be formed of materials such as, but not limited to polytetrafluoroethylene (PTFE), expanded polytetrafluoroethylene (ePTFE), polyethylene terephthalate (PET), polyethylene terephthalate polyester (PETP), purified terephthalic acid (PTA), or other materials suitable for the purposes described herein.

Figure 6A:
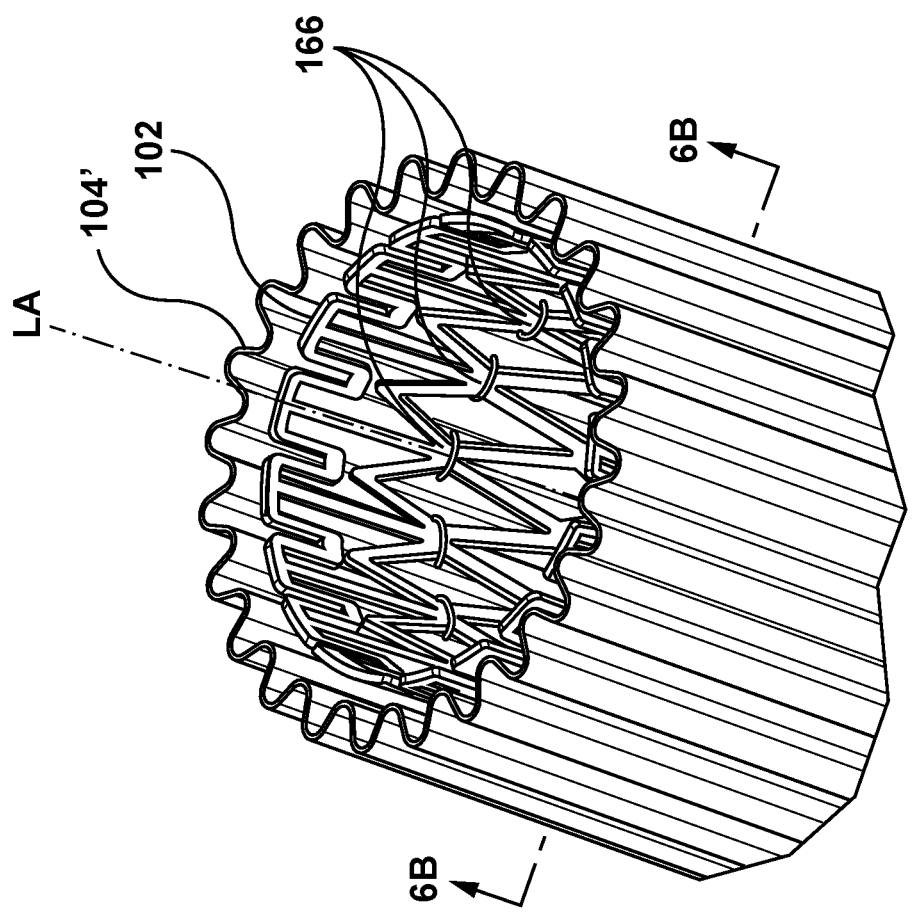
FIG. 6A is a partial perspective illustration of a sleeve of the delivery device of FIG. 3 in accordance with another embodiment hereof.
Figure 6B:
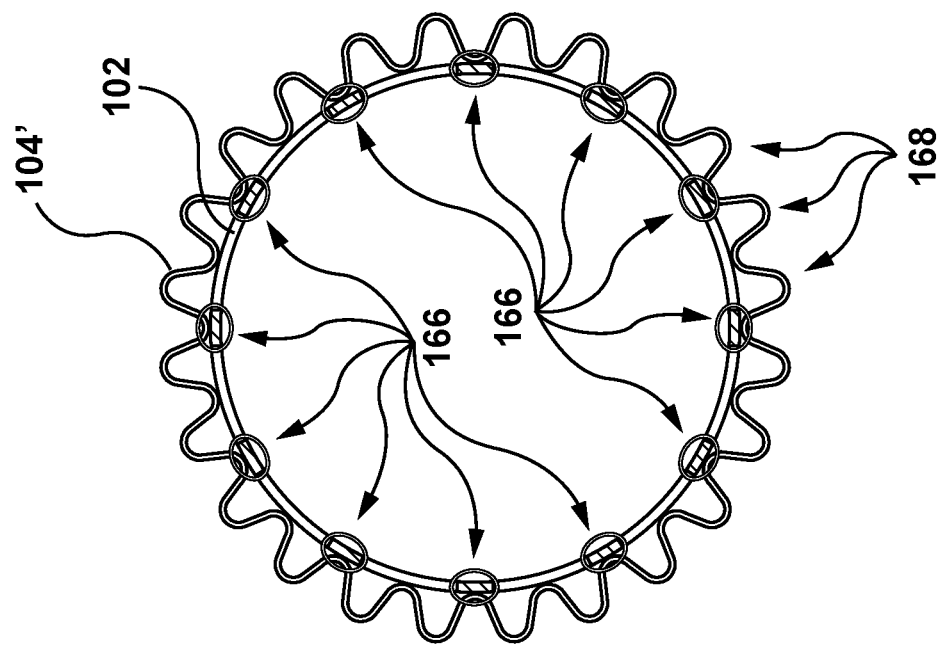
FIG. 6B is a cross-sectional illustration of the sleeve taken at line 6B-6B of FIG. 6A.
Figure 6C:
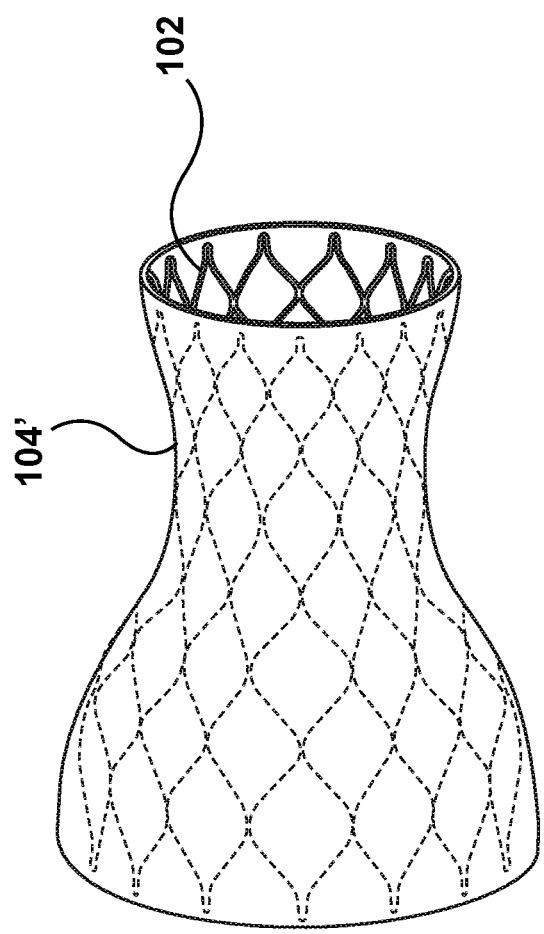
FIG. 6C is a perspective illustration of the sleeve of FIG. 6A in the deployed state.

In another embodiment, in order for the sleeve to be radially expandable from the delivery state to the deployed state, a sleeve 104' is a wavy wrap disposed around or about the outer surface of the valve prosthesis 102 in the compressed configuration, as shown in FIG. 6A and FIG. 6B and in the expanded configuration in FIG. 6C. In an embodiment, the sleeve 104' includes a generally sinusoidal outer surface extending over the length of the outer surface of the valve prosthesis 102 in the compressed configuration. A plurality of sinusoidal peaks 168 extend radially outward from the valve prosthesis 102, with each peak 168 aligned longitudinally, or parallel with the longitudinal axis LA. While the example of FIGS. 5A-5B show the sleeve 104' with twenty-four (24) sinusoidal peaks 168 when in the delivery state, this is not meant to limit the design and other configurations may be utilized. The wavy outer surface of the sleeve 104' is configured to evenly expand radially from the delivery state to the deployed state with respect to the longitudinal axis LA of the valve prosthesis 102. Thus, as the valve prosthesis 102 transforms from the compressed configuration to the expanded configuration, the sleeve 104' disposed thereon is configured such that the wavy outer surface of the sleeve 104' smoothes out or flattens as the sleeve 104' transforms from the delivery state to the deployed state. FIG. 5C shows the smoothed-out outer surface of the sleeve 104' in the deployed state over the valve prosthesis 102 in the expanded configuration. FIG. 6C shows the sleeve 104'' with a smooth outer surface in the deployed state over the valve prosthesis 102 in the expanded configuration. In an embodiment, the sleeve 104' is coupled to the valve prosthesis 102 such that the sleeve 104' will not slide or translate or migrate or otherwise undesirably move relative to the valve prosthesis 102 during delivery and deployment (due to the slippery nature of the sleeve 104'). More specifically, the sleeve 104' is coupled to the valve prosthesis 102 such that the sleeve 104' maintains proper position over the outer surface of the valve prosthesis 102 when in either the delivery or the deployed state. In an embodiment, the sleeve 104' is coupled to the valve prosthesis 102, for example, by twelve (12) axial sleeve-anchoring sutures 166 (FIG. 6B) however, more or fewer sleeve-anchoring sutures 166 may be utilized. While described in the example as including sleeve-anchoring sutures 166 to couple the sleeve 104' to the valve prosthesis 102, this is not meant to be limiting and the sleeve 104' may be coupled to the valve prosthesis by other methods, non-limiting examples of which include bonding, adhesives, wire, or other methods suitable for the purposes described herein. The sleeve 104' is a structure that allows the sleeve 104 to stretch or expand to the deployed state when the valve prosthesis 102 in the expanded configuration is disposed therein. In an embodiment, the sleeve 104' is of an elastic material. Alternatively, in may be of a shape memory material with a pre-set shape in the radially collapsed wavy delivery state. A desired radial stiffness of the sleeve 104' may be provided using variations in the structure and/or density of the shape memory material. The shape memory sleeve 104' is configured to return to the delivery state when not acted upon by an outside force (e.g. the valve prosthesis 102 in the expanded configuration). The sleeve 104' may be formed of materials such as, but not limited to polytetrafluoroethylene (PTFE), expanded polytetrafluoroethylene (ePTFE), polyethylene terephthalate (PET), polyethylene terephthalate polyester (PETP), purified terephthalic acid (PTA), or other materials suitable for the purposes described herein.

Figure 7A:
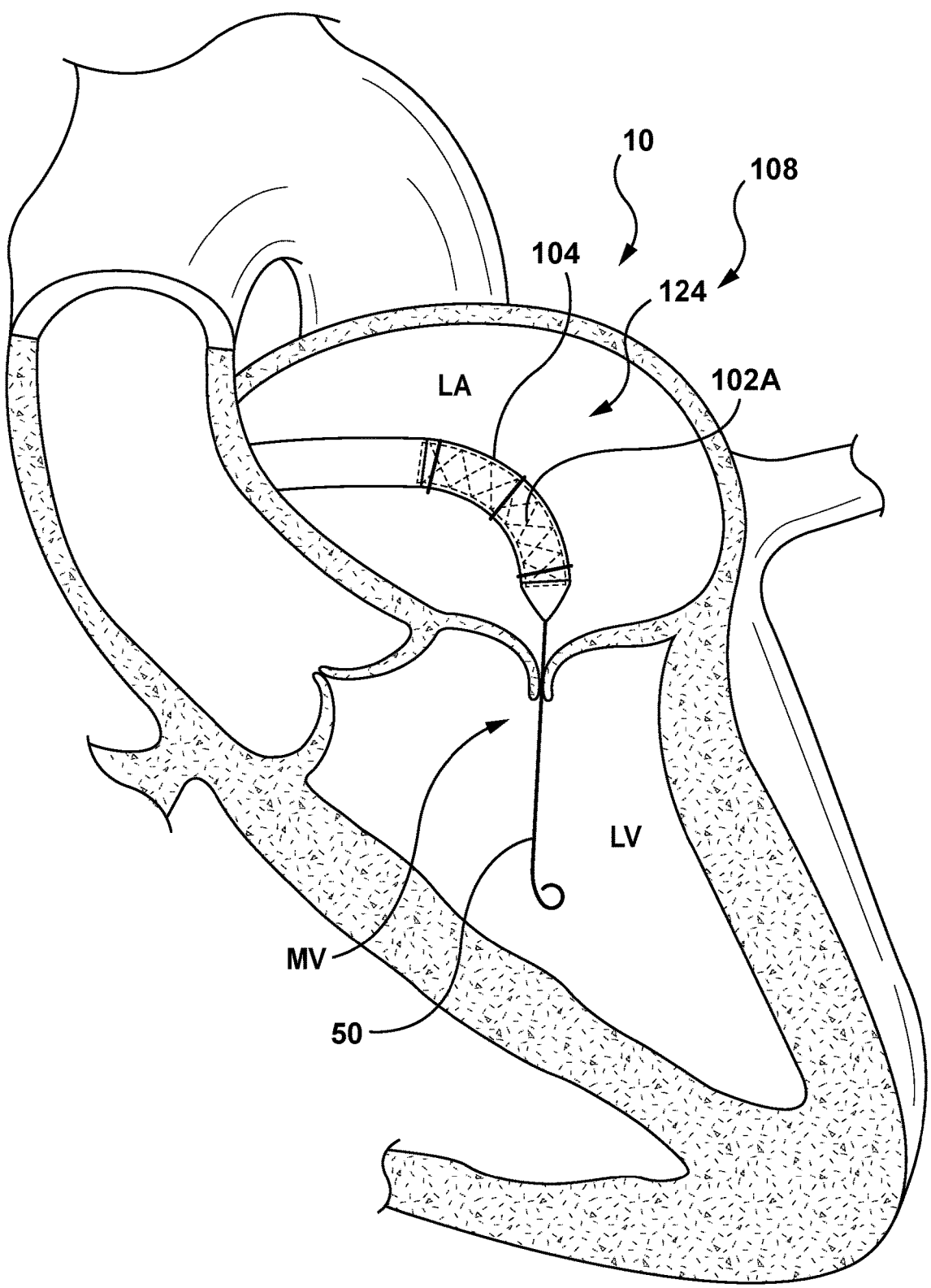
FIG. 7A is a sectional cut-away illustration of the heart illustrating a method step of using the delivery system of FIG. 3 to deliver and position a mitral valve prosthesis within a native mitral valve using a transeptal approach in accordance with an embodiment hereof, wherein the delivery system of FIG. 3 is shown being advanced to the native mitral valve.
Figure 7B:
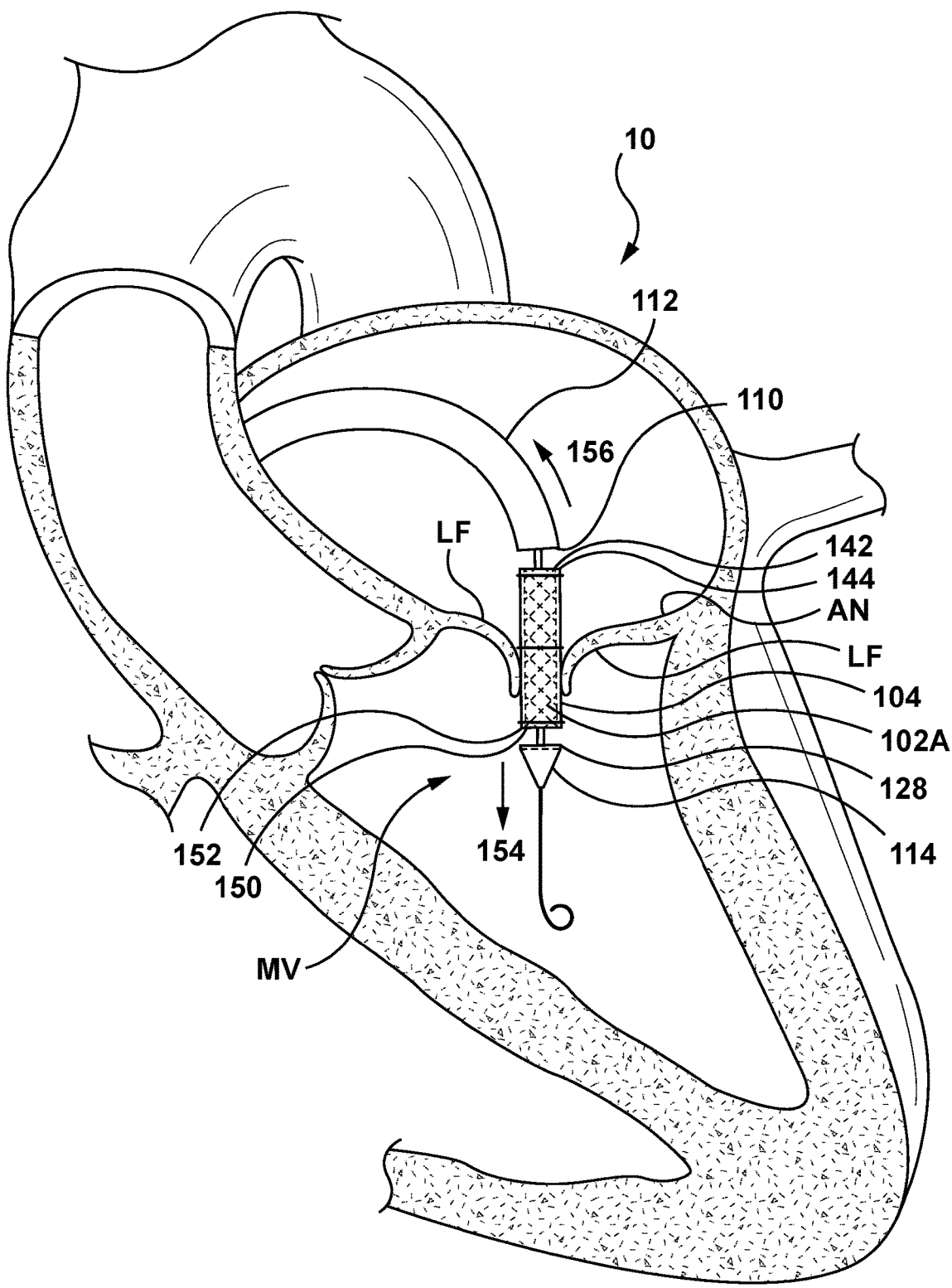
FIG. 7B is a sectional cut-away illustration of the heart illustrating a method step of using the delivery system of FIG. 3 to deliver and position a mitral valve prosthesis within a native mitral valve using a transeptal approach in accordance with an embodiment hereof, wherein the delivery system of FIG. 3 is shown positioned within the native mitral valve and a distal tip of the delivery system is advanced in the distal direction and the outer shaft of the delivery system is retracted in a proximal direction.
Figure 7C:
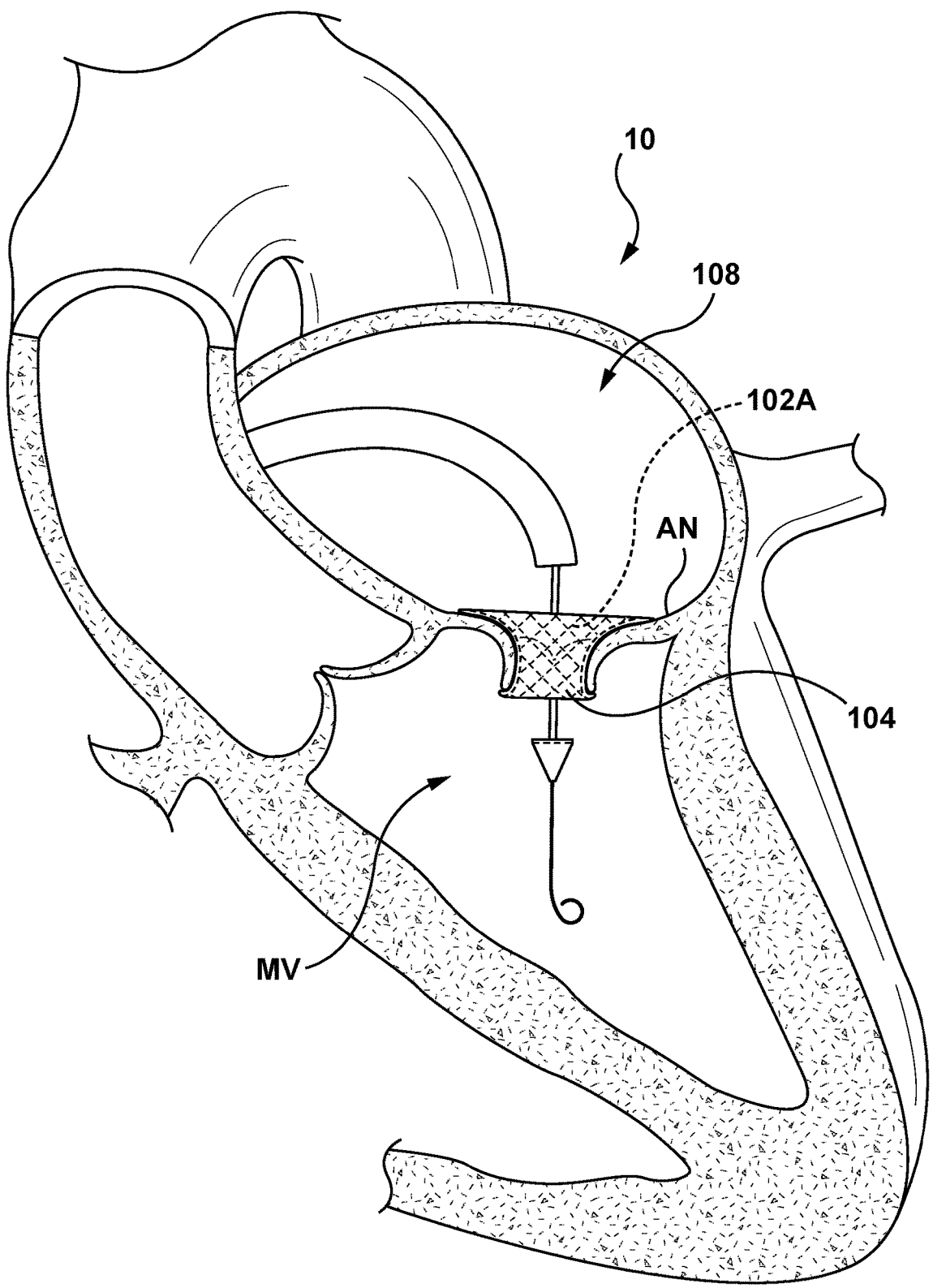
FIG. 7C is a sectional cut-away illustration of the heart illustrating a method step of using the delivery system of FIG. 3 to deliver and position a mitral valve prosthesis within a native mitral valve using a transeptal approach in accordance with an embodiment hereof, wherein a cinching mechanism of the delivery system of FIG. 3 has been actuated to radially expand the mitral valve prosthesis.

FIGS. 7A-7C are sectional cut-away views of heart 10 illustrating a transeptal approach for delivering and positioning a mitral valve prosthesis 102A using the delivery system 100 of FIGS. 3-4D and in accordance with an embodiment hereof. Referring to FIG. 7A, the distal segment 124 of the delivery catheter 108 is shown positioned in the left atria LA with the mitral valve prosthesis 102A in the compressed configuration within the sleeve 104 in the delivery state. Intravascular access to the right atria RA may be achieved via a percutaneous access site in a femoral, brachial, radial, or axillary artery. With additional reference to FIG. 3, and as will be understood by those knowledgeable in the art, the handle component 118, as well as some length of a proximal segment of the delivery catheter 108, are exposed externally of the patient for access by a clinician, even as the mitral valve prosthesis 102A and the sleeve 104 have been advanced fully to the targeted site (e.g., left atria LA) in the patient. By manipulating the handle component 118 of the delivery catheter 108 from outside the vasculature, a clinician may advance and remotely manipulate and steer the distal segment 124 of the delivery catheter 108 through the sometimes tortuous intravascular path.

Distal segment 124 of the delivery catheter 108 may be advanced into the left atria LA and positioned generally above (e.g., upstream) of the mitral valve MV. Optionally, and as shown in FIG. 7A, a guidewire 50 may be used over which the delivery catheter 108 may be slidably advanced. In a next delivery step shown in FIG. 7B, the delivery catheter 108 is advanced into proximity to and/or apposition with the mitral valve annulus AN and/or leaflets LF. Once the mitral valve prosthesis 102A is positioned within the mitral valve MV, the handle component 118 (not shown in FIGS. 7A-7C) is actuated such that the distal tip 114 is advanced in the distal direction (along arrow 154, as described previously with reference to FIG. 4C), and the outer shaft 112 is retracted in a proximal direction (along arrow 156, as described previously with reference to FIG. 4C) such that the first end 142 of the valve prosthesis 102 and/or the first end 144 of the sleeve 104 are no longer retained within the circumferential recess 146 of the distal end 110 of the outer shaft 112, and the second end 150 of the valve prosthesis 102 and/or the second end 152 of the sleeve 104 are no longer retained within the circumferential recess 148 of the proximal end 128 of the distal tip 114, respectively. Once the valve prosthesis 102A and the sleeve 104 are no longer disposed within the recesses 146, 148 of the outer shaft 112 and the distal tip 114, respectively, the cinching assembly 116 is actuated. Actuation of the cinching assembly 116 as previously described with respect to FIGS. 4A-4B provides slack or releases the cinching sutures 138 thereby allowing the mitral valve prosthesis 102A to self-expand to the expanded configuration. Expansion of the mitral valve prosthesis 102A also expands the sleeve 104 from the delivery state to the deployed state, as shown in FIG. 7C. With the mitral valve prosthesis 102A in the expanded configuration and the sleeve 104 in the deployed state within the annulus of the native mitral valve MV, the sleeve 104 is disposed between or embedded the wall of the native mitral valve MV and the mitral valve prosthesis 102A along the full length of the mitral valve prosthesis 102A.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of the mitral valve prosthesis 102A at the target native valve region. In another embodiment, selected outer surfaces of the distal segment 124 may be treated such that the echogenicity of the distal segment 124 is enhanced. In some embodiments, image guidance components (e.g., IVUS, OCT) may be coupled to the distal segment 124 of the delivery catheter 108 to provide three-dimensional images of the vasculature proximate to the target heart valve region to facilitate positioning, orienting and/or deployment of the mitral valve prosthesis 102A within the heart valve region.

Following delivery, placement and implantation of the mitral valve prosthesis 102A within the mitral valve MV (or other desired valve location), the delivery catheter 108 and remaining guidewire (if any) may be removed from the heart and out of the body of the patient, as would be understood by one of skill in the art.

Figure 8:
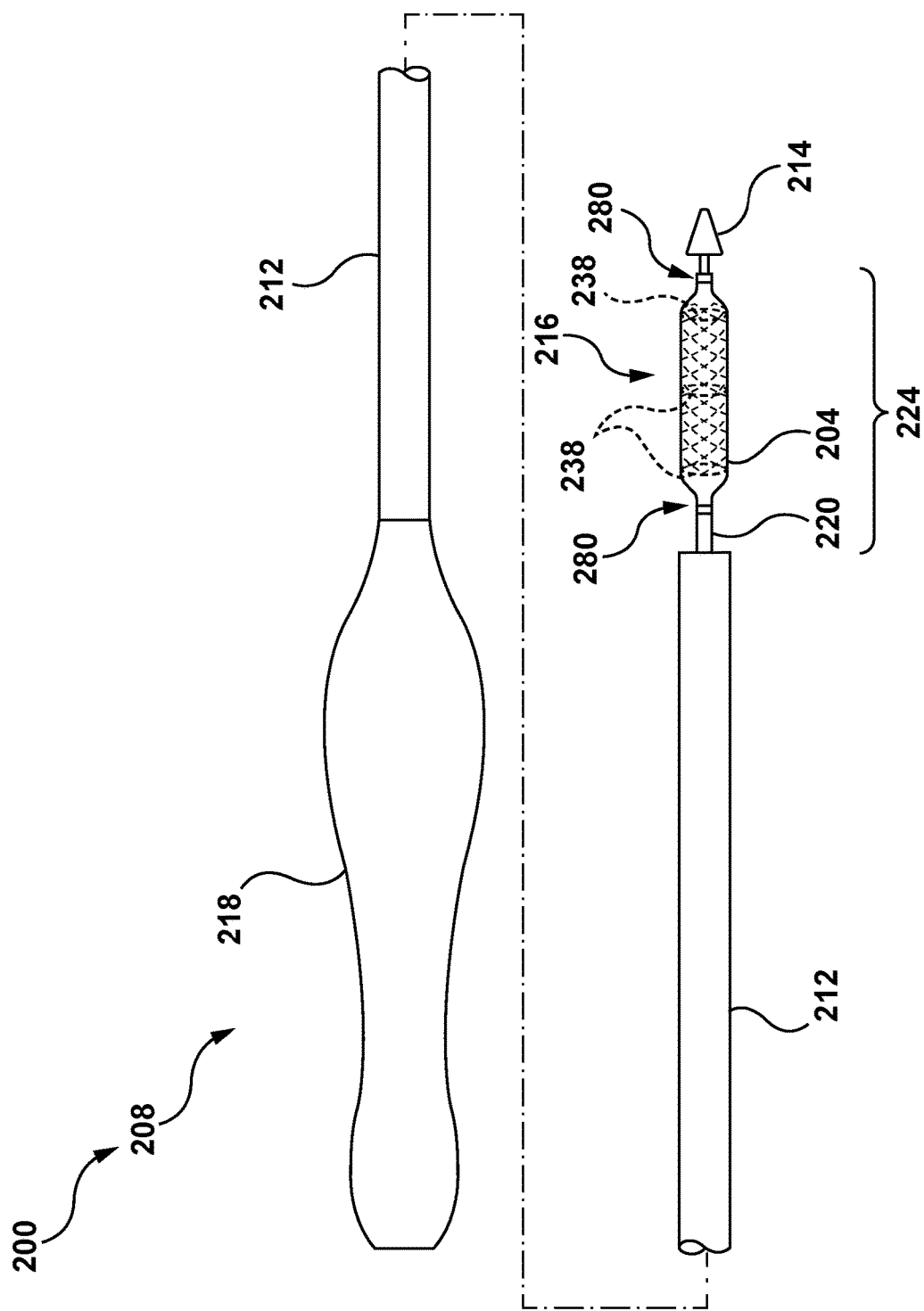
FIG. 8 is a side illustration of a minimally invasive heart valve prosthesis delivery system configured in accordance with an embodiment hereof.
Figure 9A:
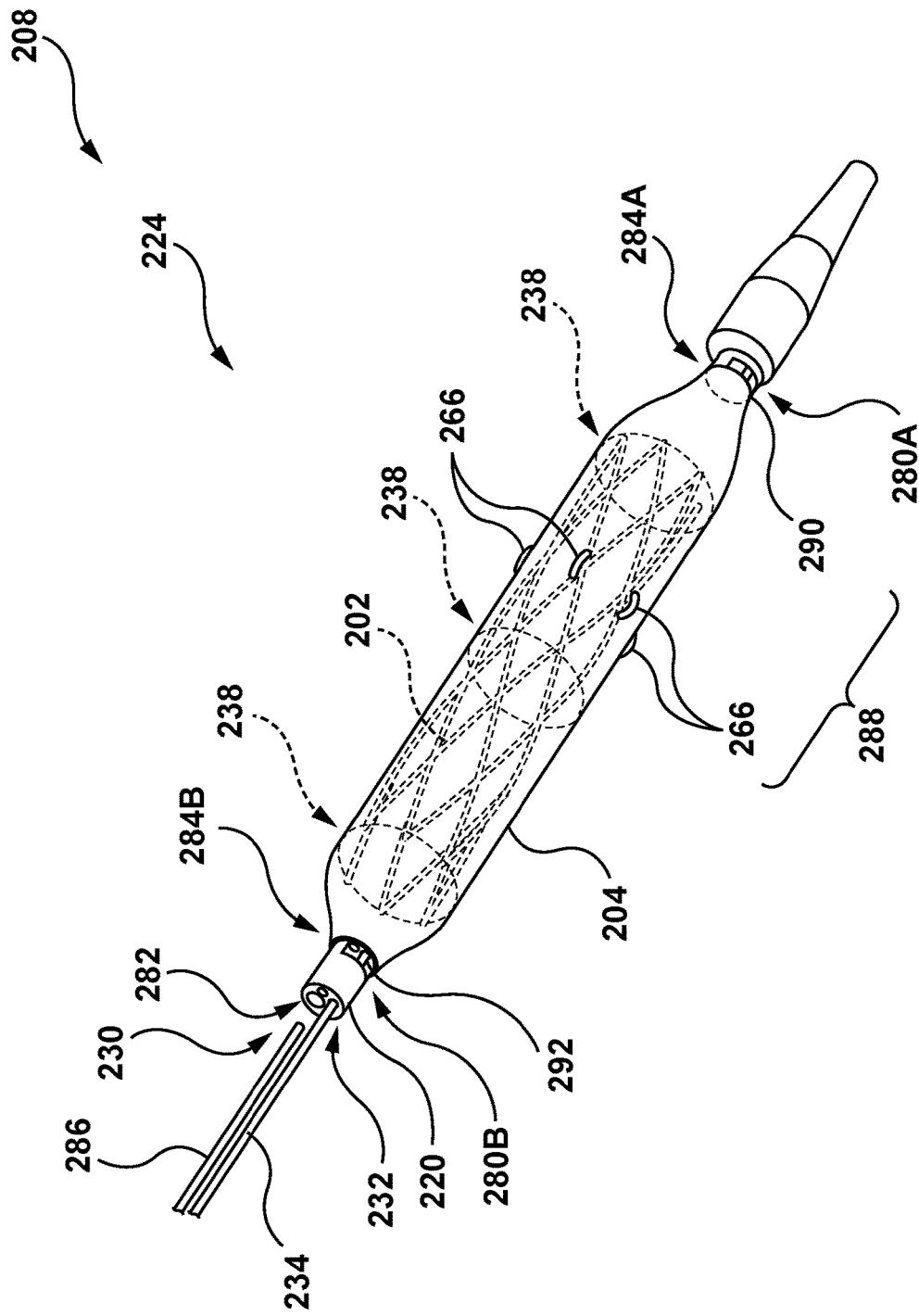
FIG. 9A is a partial perspective illustration of a distal portion of the delivery system of FIG. 8 with a valve prosthesis in the compressed configuration in accordance with another embodiment hereof.
Figure 9C:
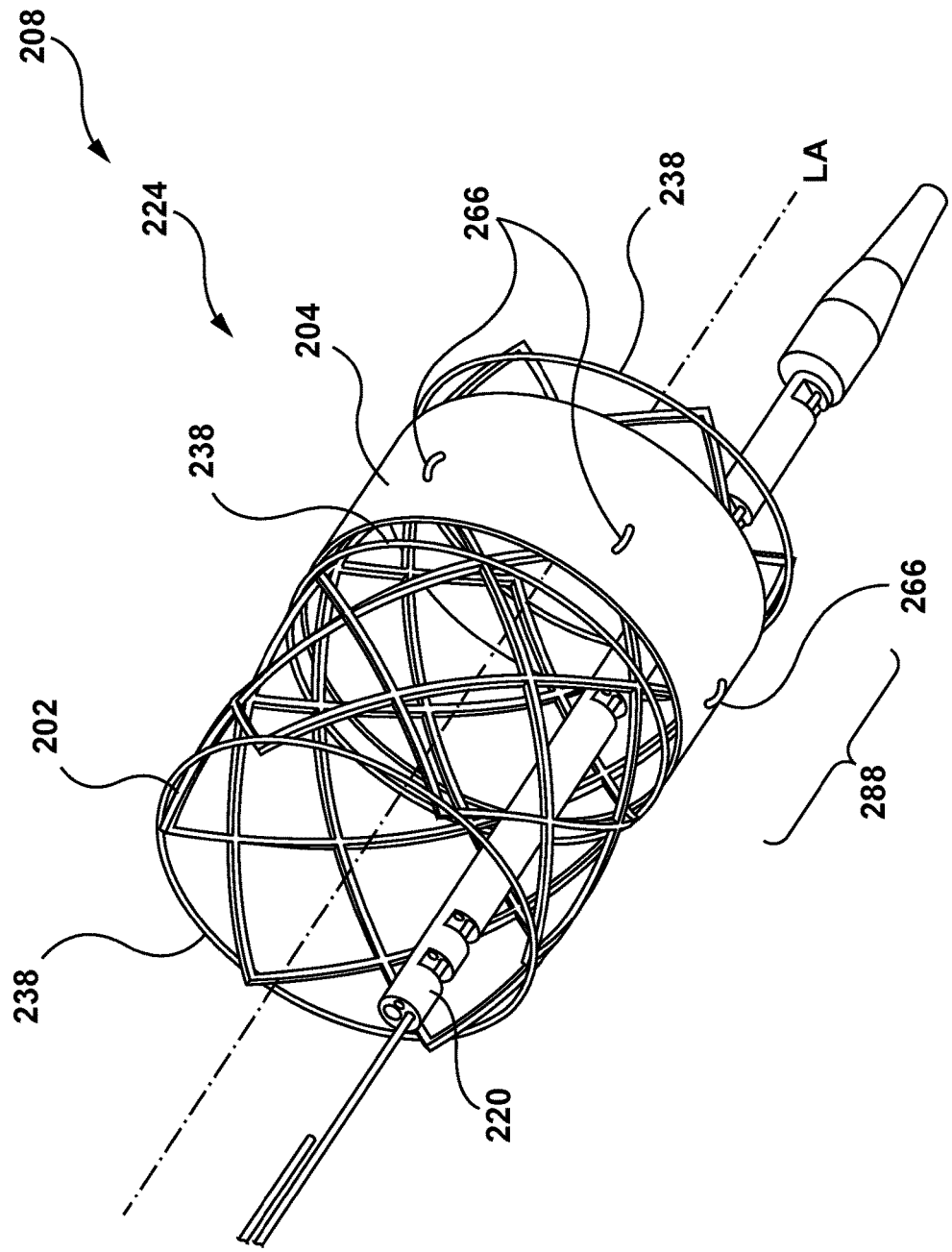
FIG. 9C is a perspective illustration of the distal portion of the delivery device of FIG. 9A with the valve prosthesis in the expanded configuration.

FIG. 8 is a side view of a minimally invasive heart valve prosthesis delivery system 200 (hereinafter referred to as "delivery system 200") configured in accordance with another embodiment hereof for delivery of a heart valve prosthesis 202 (hereafter referred to as "valve prosthesis 202" for sake of simplicity). FIGS. 9A-9C are enlarged partial sectional views of a distal segment 224 of a delivery catheter 208 for use with the heart valve prosthesis delivery system 200 of FIG. 8 shown in a delivery state, an intermediate or transforming state, and a deployed state, respectively, and in accordance with an embodiment hereof. The delivery catheter 208 includes features generally similar to the features of the delivery catheter 108 described above with reference to FIGS. 3-6D. For example, the delivery catheter 208 includes a handle 218, an elongated shaft component 220, an outer shaft 212, a cinching assembly 216, and a distal tip 214. Therefore, many of the construction details and alternatives of the delivery catheter 208 will not be repeated with respect to the present embodiment. Further, the valve prosthesis 202 includes features generally similar to the features of the valve prosthesis 102 described above with reference to FIGS. 3-6D. However, in the embodiment of FIGS. 8-9C, a radially-expandable sleeve 204 (hereafter referred to as "sleeve 204" for sake of simplicity) is releasably coupled to the delivery catheter 208 by at least one sleeve-restraining suture 280 when the sleeve 204 is in a delivery state. Additionally, the sleeve 204 is configured to contract longitudinally when expanded radially, as described in greater detail below, such that the sleeve 204 extends over only a portion of the length of the valve prosthesis 202 in the expanded configuration.

In the embodiment illustrated in FIGS. 9A-9C, the cinching assembly 216 is configured to releasably compressively constrain the valve prosthesis 202 similar to the cinching assembly 116 described previously with respect to FIGS. 3-4C. Examples of suitable cinch assemblies for retaining self-expanding valve prostheses are described in U.S. Patent Publication No. 2014/0330368 to Gloss, previously incorporated herein by reference in its entirety. In this embodiment, the cinching assembly 216 includes three (3) cinching sutures or suture loops 238, as shown in FIG. 9A. In this embodiment, each cinching suture 238 encircles or extends circumferentially around an outer surface of the valve prosthesis 202 and within an inner surface of the sleeve 204 such that the cinching sutures 238 constrain the valve prosthesis 202 in the compressed configuration. Stated more plainly, each cinching suture 238 is disposed between the valve prosthesis 202 and the sleeve 204. In another embodiment (not shown), each cinching suture 238 may extend circumferentially around the outer surface of the sleeve 204 and the valve prosthesis 202 disposed therein.

The elongated shaft component 220 is similar to the elongated shaft component 120, described previously, however the elongated shaft component 220 of the delivery catheter 208 further includes a sleeve lumen 282 (shown in FIG. 9A) and at least one sleeve notch 284 (sleeve notches 284A, 284B also shown in FIG. 9A and described in more detail below). Thus, the elongated shaft component 220 includes a guidewire lumen 230, a cinch lumen 232, and the sleeve lumen 282. In other embodiments, the elongated shaft component 120 may include more or fewer lumens based upon the application. The guidewire lumen 230 is configured to slidably receive a guidewire (not shown) therein. The cinch lumen 232 is configured to slidably receive a cinch release pin 234 therein. The sleeve lumen 282 is configured to slidably receive a sleeve release pin 286 therein, as described in greater detail below. In the embodiment of FIGS. 9A-9C, the elongated shaft component 220 includes a first sleeve notch 284A at a distal portion of the distal segment 224, and a second sleeve notch 284B at a proximal portion of the distal segment 224. The first and second sleeve notches 284A, 284B are openings in the outer wall of the elongated shaft component 220 extending from an outer surface to an inner surface, there through for access to the sleeve lumen 282. While shown in FIGS. 9A-9C with two (2) sleeve notches 284A, 284B at specific locations of the elongated shaft component 220, in other embodiments more or at least one sleeve notches/notch 284 at various locations along the distal segment 224 of the elongated shaft component 220 may be utilized.

Similar to the sleeve 104 and the valve prosthesis 102, the sleeve 204 is coupled to the valve prosthesis 202 by the sleeve anchoring sutures 266 such that the sleeve 204 is integrated onto the valve prosthesis 202. More specifically, the sleeve anchoring sutures 266 couple the sleeve 204 to the valve prosthesis 202 when the sleeve 204 is in either the delivery or the deployed state. The sleeve 204 is further releasably coupled to the elongated shaft component 220 of the delivery catheter 208 by sleeve-retaining sutures 280A and 280B, described in greater detail below, when the sleeve 204 is in the delivery state. FIG. 9A shows the valve prosthesis restrained in the compressed configuration by the restraining sutures 238 and the sleeve 204 in the delivery state and releasably coupled to the elongated shaft component 220 by the sleeve restraining sutures 280A and 280B. FIG. 9B shows the valve prosthesis expanding radially outward and in transformation from the compressed configuration to the expanded configuration. FIG. 9B further shows the sleeve 204 coupled to the valve prosthesis 202 by the sleeve anchoring sutures 266 and in transformation from the delivery state to the deployed state. In FIG. 9B, the sleeve restraining sutures 280A and 280B have been released and the sleeve 204 is coupled only to the valve prosthesis 202 by the sleeve anchoring sutures 266. Further, the restraining sutures 238 are controllably released in FIG. 9B, with the restraining sutures 238 controlling the expansion of the valve prosthesis 202 and the sleeve 204 coupled thereto. FIG. 9C shows the valve prosthesis 202 in the expanded configuration and the sleeve 204 in the expanded state coupled thereto.

In an embodiment, in order for the sleeve 204 to be radially expandable from the delivery state to the deployed state, the sleeve 204 is formed from an elastic or resilient material. More particularly, the sleeve 204 is of an elastic or resilient material of knitted, woven, or mesh construction that is stretched over the valve prosthesis 202 in the compressed configuration, non-limiting examples of which include polytetrafluoroethylene (PTFE), expanded polytetrafluoroethylene (ePTFE), polyethylene terephthalate (PET), or other materials suitable for the purposes described herein. Alternatively, the sleeve 204 may be a ring constructed of silicone or an elastic urethane. When the valve prosthesis 202 self-expands and applies an outward radial force to the sleeve 204, the elastic or resilient nature of the sleeve 204 allows the sleeve 204 to radially expand to the deployed state and also allows the sleeve 204 to contract or shrink longitudinally as the sleeve 204 expands radially. Thus, in this embodiment, self-expansion of the valve prosthesis 202 as well as the elastic or resilient nature of the sleeve 204 cause the sleeve 204 to transform between the delivery state and the deployed state. Since the sleeve 204 contracts or shrinks longitudinally as it radially expands, the sleeve 204 covers the full length of the valve prosthesis 202 when in the delivery state (shown in FIG. 9A) and only a portion of the length of the valve prosthesis 202 when in the deployed state (shown in FIG. 9C). In embodiments in which the sleeve 204 is a knitted, woven, or mesh material, it may be advantageous to dispose the distalmost and proximalmost cinching sutures 238 about or encircling the inflow and outflow crowns of the valve prosthesis 202, as shown in FIG. 8 and FIGS. 9A-9C, such that upon release of the sleeve-retaining sutures 280A and 280B the sleeve 204 does not snag, become entangled with, or hang-up on the crowns of the valve prosthesis 202.

In another embodiment, the sleeve 204 may be of a compliant but non-resilient material (or less resilient material) and longitudinal contraction of the sleeve 204 during transformation to the delivery state may be accomplished by other methods, such as, but not limited to activation of sutures (not shown) configured to pull the sleeve 204 to the contracted state, or other methods suitable for the purposes described herein. More particularly, the sleeve 204 is compliant but non-resilient material of knitted, woven, or mesh construction that is stretched over the valve prosthesis 202 in the compressed configuration, non-limiting examples of which include polytetrafluoroethylene (PTFE), expanded polytetrafluoroethylene (ePTFE), polyethylene terephthalate (PET), or other materials suitable for the purposes described herein.

As previously stated, the sleeve 204 is releasably coupled to the delivery catheter 208 of the delivery system 200 by at least one removable sleeve-restraining suture 280. In an embodiment, the delivery catheter 208 includes first sleeve-restraining suture 280A at a first end 290 of the sleeve 204 and second sleeve-restraining suture 280B at a second end 292 of the sleeve 204, as shown in FIG. 9A. Each sleeve-restraining suture 280 encircles or extends circumferentially around an outer surface of the sleeve 204 such that the sleeve-restraining sutures 280 constrain sleeve 204 about the valve prosthesis 102 in the compressed configuration. Further, each sleeve-restraining suture 280 when so disposed at the first end 290 and the second end 292, releasably couples the sleeve 204 to the elongated shaft component 220 and thus to the delivery catheter 208. Each sleeve-restraining suture 280 further extends through the respective sleeve notch 284 and couples with the sleeve release pin 286 disposed within the sleeve lumen 282 of the elongated shaft component 220. The sleeve release pin 286 is operably coupled to the handle 218 at a proximal end thereof (not shown) and is slidable or translatable relative to the elongated shaft component 220. The sleeve release pin 286 and the sleeve-restraining sutures 280 coupled thereto are configured such that remote actuation of the sleeve release pin 286 (e.g., via an actuator such as a knob, pin, or lever carried by the handle component 218) with the valve prosthesis 202 in the compressed configuration controllably releases the sleeve-restraining sutures 280 from the elongated shaft component 220 such that the sleeve 204 may transform from the delivery state to the deployed state upon radial expansion of the valve prosthesis 102, disposed therein as described above. Stated another way, when in the delivery state, the sleeve 204 is stretched tightly over the valve prosthesis 202 and the elongated shaft component 220. Thus, the sleeve 204 is configured to or functions as a cover that prevents damage to the vasculature as the valve prosthesis 202 is advanced through a patient, and is further configured to be releasable from the elongated shaft component 220 to function as a sealing component after the valve prosthesis 202 is radially expanded to the expanded configuration within the annulus of a target valve.

In an embodiment shown in FIGS. 9A-9C, the sleeve 204 is coupled to the valve prosthesis 202 by six (6) sleeve-anchoring sutures 266. Sleeve-anchoring sutures 266 are similar to sleeve-anchoring sutures 166 described previously, and therefore they will not be described here in detail. In other embodiments, more or fewer sleeve-anchoring sutures 266 may be used based upon the application. In still other embodiments, the sleeve 204 may be coupled to the valve prosthesis by other methods such as, but not limited to bonding, adhesives, or other methods suitable for the purposes disclosed herein.

The sleeve-anchoring sutures 266 hold a portion of the sleeve 204 adjacent to each sleeve-anchoring suture 266 in position with respect to the valve prosthesis 202. When anchored thusly, as the sleeve 204 expands due to the outward radial force applied thereto by the valve prosthesis 202 transforming from the compressed to the expanded configuration, the sleeve 204 contracts longitudinally as it transforms from the delivery state to the deployed state, and the final position of the sleeve 204 relative to the valve prosthesis 202 may be controlled by the position of the sleeve-anchoring sutures 266. As shown in FIG. 9A, the sleeve-anchoring sutures 266 are disposed at the end portion 288 of the valve prosthesis 202. When the valve prosthesis 202 expands to the expanded configuration as shown in FIG. 9B and FIG. 9C, the sleeve 204 radially expands and longitudinally contracts to the deployed state and the final location of the sleeve 204 is at the end portion 288 of the valve prosthesis 202 (the inflow-end portion when the valve prosthesis 202 is configured for an aortic approach to an aortic valve). Thus, in the deployed state, the final position of the sleeve 204 is determined by the location of the sleeve-anchoring sutures 266.

Figure 10A:
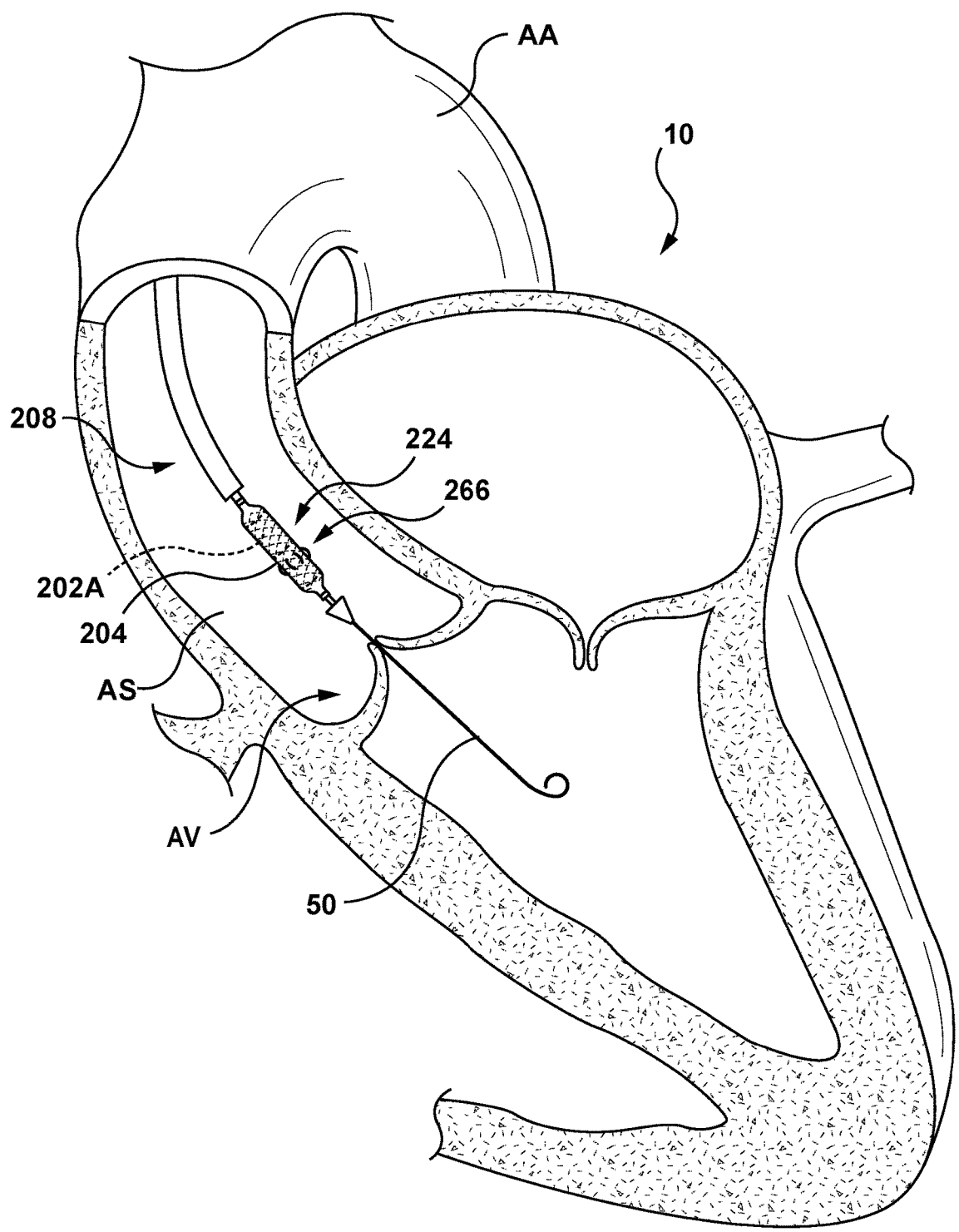
FIG. 10A is a sectional cut-away illustration of the heart illustrating a method step of using the delivery system of FIG. 8 to deliver and position an aortic valve prosthesis within a native aortic valve using an aortic approach in accordance with another embodiment hereof, wherein the delivery system of FIG. 8 is shown being advanced to the native mitral valve.
Figure 10B:
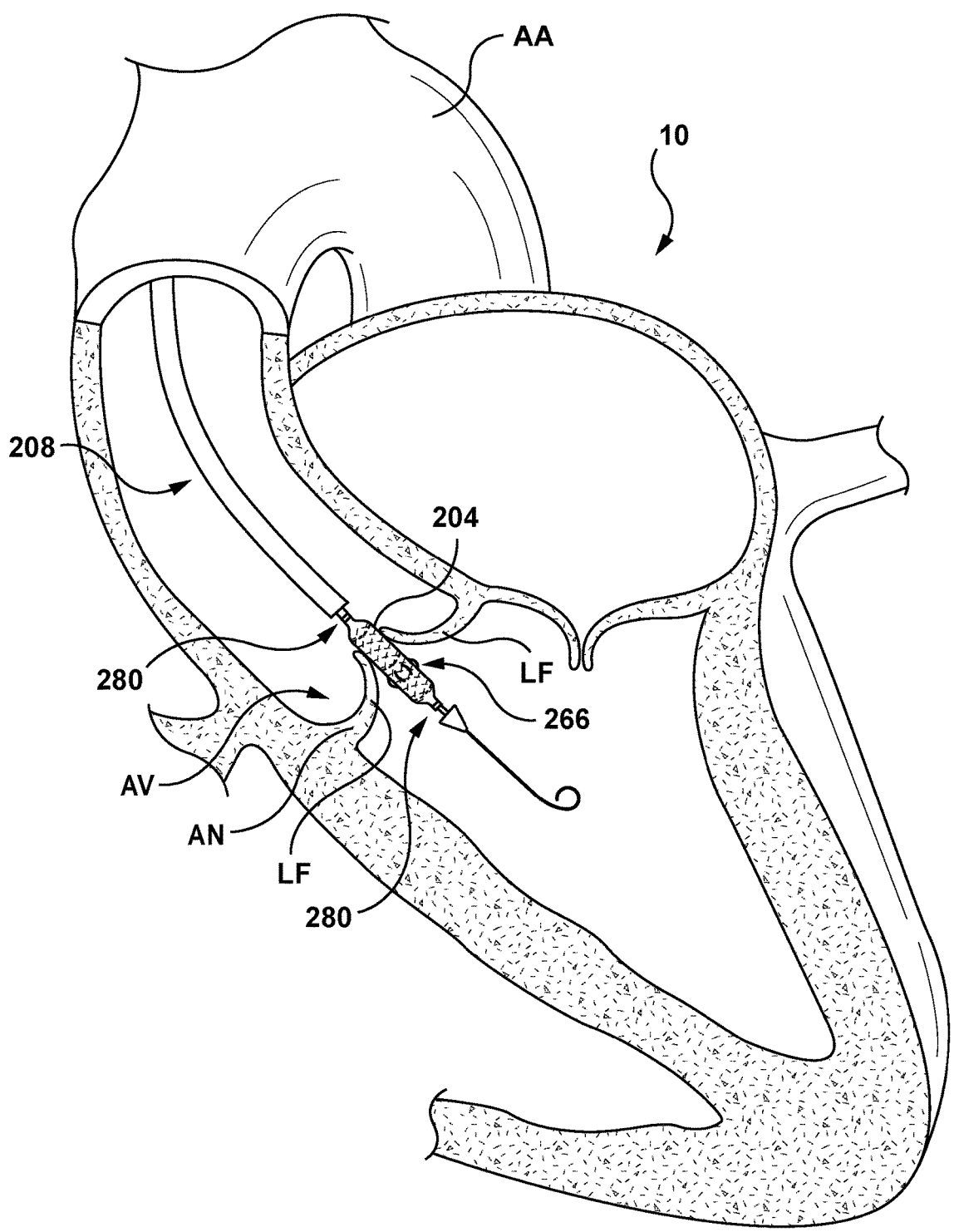
FIG. 10B is a sectional cut-away illustration of the heart illustrating a method step of using the delivery system of FIG. 8 to deliver and position an aortic valve prosthesis within a native aortic valve using an aortic approach in accordance with another embodiment hereof, wherein the delivery system of FIG. 8 is shown positioned within the native aortic valve.
Figure 10C:
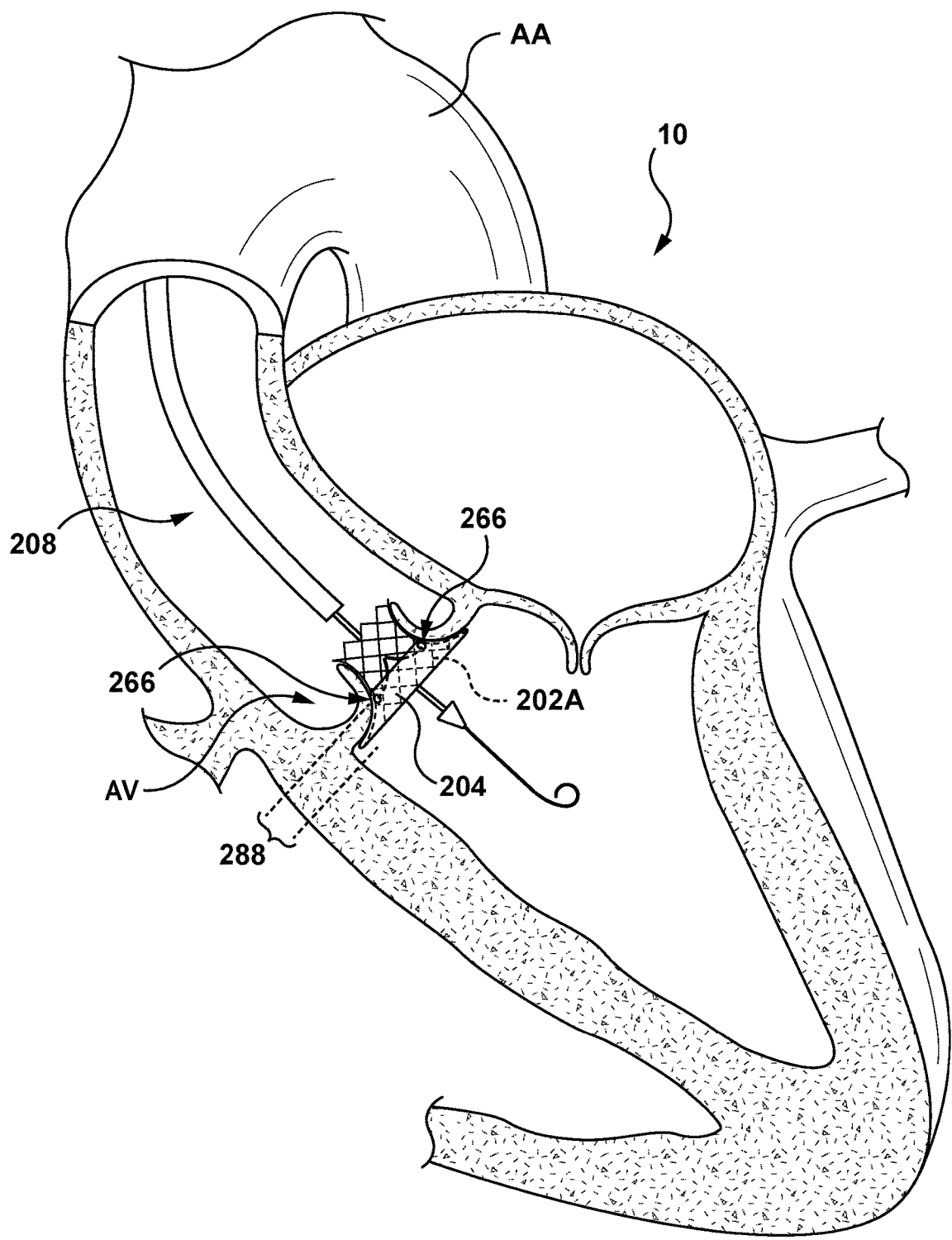
FIG. 10C is a sectional cut-away illustration of the heart illustrating a method step of using the delivery system of FIG. 8 to deliver and position an aortic valve prosthesis within a native aortic valve using an aortic approach in accordance with another embodiment hereof, wherein sleeve-restraining sutures of the delivery system of FIG. 8 have been removed and a cinching mechanism of the delivery system of FIG. 8 has been actuated to radially expand the aortic valve prosthesis.

FIGS. 10A-10C are sectional cut-away views of a heart 10 illustrating an aortic approach for delivering and positioning an aortic valve prosthesis 202A using the delivery system 200 of FIGS. 8-9C and in accordance with an embodiment hereof. Referring to FIG. 10A, the distal segment 224 of the delivery catheter 208 is shown positioned in the aorta A with the aortic valve prosthesis 202A in the compressed configuration within the sleeve 204 in the delivery state. Intravascular access to the aortic valve AV may be achieved via a percutaneous access site in a femoral, brachial, radial, or axillary artery. With additional reference to FIG. 8, and as will be understood by those of skill in the art, the handle component 218, as well as some length of a proximal segment of the delivery catheter 208, are exposed externally of the patient for access by a clinician, even as the aortic valve prosthesis 202A and the sleeve 204 have been advanced fully to the targeted site (e.g., aortic sinus) in the patient. By manipulating the handle component 218 of the delivery catheter 208 from outside the vasculature, a clinician may advance and remotely manipulate and steer the distal segment 224 of the delivery catheter 208 through the sometimes tortuous intravascular path.

Distal segment 224 of the delivery catheter 208 may be advanced through the aortic arch AA and into the aortic sinus AS and positioned generally above (e.g., downstream) of the aortic valve AV. Optionally, and as shown in FIG. 10A, a guidewire 50 may be used over which the delivery catheter 208 may be slidably advanced. In a next delivery step shown in FIG. 10B, the delivery catheter 208 is advanced into proximity to and/or apposition with the aortic valve annulus AN and/or leaflets LF. Once the aortic valve prosthesis 202A is positioned within the aortic valve AV, the handle 218 is actuated such that the sleeve-restraining sutures 280 are released. The sleeve 204 is now coupled only to the aortic valve prosthesis 202A by the sleeve-anchoring sutures 266. Once the sleeve-restraining sutures 280 are released, the handle 218 is actuated such that cinching assembly 216 provides slack or releases the cinching sutures 238 thereby allowing the aortic valve prosthesis 202A to transform to the expanded configuration. Expansion of the aortic valve prosthesis 202A expands the sleeve 204 from the delivery state to the deployed state, wherein as the sleeve 204 expands radially, the sleeve 204 also contracts longitudinally along the longitudinal axis LA of the aortic valve prosthesis 202A, and around the sleeve-anchoring sutures 266, as described with respect to FIG. 9C. With the aortic valve prosthesis 202A in the expanded configuration and the sleeve 204 in the deployed state within the annulus of the native aortic valve AV, the sleeve 204 is disposed or embedded between the wall of the native aortic valve AV and the aortic valve prosthesis 202A at the inflow-end portion 288 of the aortic valve prosthesis 202A as shown in FIG. 10C.

Image guidance, enhanced echogenicity, or other methods as described previously with respect to the embodiment of FIGS. 3-7C may be used to aid the clinician's delivery and positioning of the aortic valve prosthesis 202A at the target native valve region.

Following delivery, placement and implantation of the aortic valve prosthesis 202A within the aortic valve AV (or other desired valve location), the delivery catheter 208 and remaining guidewire (if any) may be removed from the heart 10 and out of the body of the patient, as would be understood by one of skill in the art.

Features of the valve prosthesis delivery systems, delivery catheters and delivery catheter components described above and illustrated in FIGS. 3-6B and 8-9C may be modified to form additional embodiments configured in accordance herewith. For example, the delivery system 100 may provide delivery of any of the delivery catheters having sleeves described and illustrated in FIGS. 3-10C to a targeted heart region (e.g., left atria or aortic sinus), and may further incorporate additional delivery elements such as straightening sheaths and/or guide wires controllable, for example, using the handle component 118. Furthermore, embodiments shown configured for carrying self-expanding valve prostheses may also be configured to carry balloon-expandable valve prostheses. More particularly, sleeves 104, 104', 204 may be utilized with a balloon-expandable valve prostheses to function as a protective component during tracking or delivery and to further function as a skirt for prevention of PVL after deployment. When sleeves 104, 104', 204 are utilized with a balloon-expandable valve prostheses, cinching suture(s) 138,238 for radially compressing the valve prosthesis into the compressed configuration for delivery are not required since a balloon (not shown) is utilized for expanding the valve prosthesis. Additionally, catheter assemblies having only one guidewire lumen may be provided with more than one guidewire lumen.

Furthermore, while the delivery catheters described above are discussed as being suitable for delivering a mitral valve prosthesis to the native mitral valve using a transseptal approach and an aortic valve prosthesis to the native aortic valve using an aortic approach, it will be understood that the delivery catheters may also be suitable for delivering heart valve devices for repair and/or replacement of other heart valves (e.g., pulmonary valve, tricuspid valve, etc.) and utilizing other approaches (e.g. retrograde, antegrade). Various arrangements of the delivery catheters described herein may also be used to deliver other therapeutic or medical tools within body lumens.

Various method steps described above for delivery and positioning of valve prosthesis devices (e.g., mitral or aortic valve prostheses) within a native heart valve of a patient also may be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail may be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, may be used in combination with the features of any other embodiment. All patents and publications discussed herein are incorporated by reference herein in their entirety.

What is claimed is:

1. A delivery system for percutaneously delivering a self-expanding valve prosthesis comprising:
   an elongated shaft component;
   a self-expanding valve prosthesis disposed over a distal portion of the elongated shaft component, wherein the valve prosthesis has a compressed configuration for delivery within a vasculature and an expanded configuration for deployment;
   at least one cinching suture for coupling the valve prosthesis to the elongated shaft component, wherein the at least one cinching suture is removable and radially compresses the valve prosthesis into the compressed configuration for delivery; and
   a radially-expandable sleeve secured to and encircling an outer surface of the valve prosthesis, wherein the radially-expandable sleeve is configured to transform from a delivery state in which the radially-expandable sleeve has a first diameter and extends over a full length of the valve prosthesis in the compressed configuration to a deployed state in which the radially-expandable sleeve has a second diameter greater than the first diameter and extends over a portion of the valve prosthesis in the expanded configuration, the portion being less than the full length of the valve prosthesis, the radially-expandable sleeve being configured to prevent paravalvular leakage in situ in the deployed state.

2. The delivery system of claim 1, wherein the radially-expandable sleeve contracts longitudinally when the radially-expandable sleeve transforms from the delivery state to the deployed state such that the radially-expandable sleeve in the deployed state extends over only an inflow end portion of the valve prosthesis in the expanded configuration and lays flush against the outer surface of the valve prosthesis.

3. The delivery system of claim 2, wherein the radially-expandable sleeve is formed from an elastic material that is stretched over the valve prosthesis in the compressed configuration.

4. The delivery system of claim 3, further comprising at least one sleeve-restraining suture for coupling the radially-expandable sleeve to the delivery system, wherein the at least one sleeve-restraining suture is removable.

5. The delivery system of claim 4, wherein the at least one cinching suture is disposed between the outer surface of the valve prosthesis and an inner surface of the radially-expandable sleeve.

6. The delivery system of claim 4, wherein the at least one sleeve-restraining suture includes a first sleeve-restraining suture at a first end of the radially-expandable sleeve and a second sleeve-restraining suture at a second end of the radially-expandable sleeve.

7. The delivery system of claim 1, wherein the radially-expandable sleeve is secured to the outer surface of the valve prosthesis via at least one sleeve-anchoring suture.

8. The delivery system of claim 1, wherein the valve prosthesis includes a tubular stent and a prosthetic valve component disposed within and secured to the stent.

9. A delivery system for percutaneously delivering a self-expanding valve prosthesis comprising:
   an elongated shaft component;
   a self-expanding valve prosthesis disposed over a distal portion of the elongated shaft component, wherein the valve prosthesis has a compressed configuration for delivery within a vasculature and an expanded configuration for deployment;
   at least one cinching suture for coupling the valve prosthesis to the elongated shaft component, wherein the at least one cinching suture is removable and radially compresses the valve prosthesis into the compressed configuration for delivery; and
   a radially-expandable sleeve secured to and encircling an outer surface of the valve prosthesis, wherein the radially-expandable sleeve is configured to transform from a delivery state in which the radially-expandable sleeve has a first diameter and extends over a full length of the valve prosthesis in the compressed configuration and forms an outermost component of the delivery system for a longitudinal portion thereof to a deployed state in which the radially-expandable sleeve has a second diameter greater than the first diameter and extends over a portion of the valve prosthesis in the expanded configuration, the portion being less than the full length of the valve prosthesis, the radially-expandable sleeve being configured to prevent paravalvular leakage in situ in the deployed state.

10. The delivery system of claim 9, wherein the radially-expandable sleeve contracts longitudinally when the radially-expandable sleeve transforms from the delivery state to the deployed state such that the radially-expandable sleeve in the deployed state extends over only an inflow end portion of the valve prosthesis in the expanded configuration and lays flush against the outer surface of the valve prosthesis.

11. The delivery system of claim 10, wherein the radially-expandable sleeve is formed from an elastic material that is stretched over the valve prosthesis in the compressed configuration.

12. A delivery system for percutaneously delivering a self-expanding valve prosthesis comprising:
   an elongated shaft component;
   a self-expanding valve prosthesis disposed over a distal portion of the elongated shaft component, wherein the valve prosthesis has a compressed configuration for delivery within a vasculature and an expanded configuration for deployment;
   at least one cinching suture for coupling the valve prosthesis to the elongated shaft component, wherein the at least one cinching suture is removable and radially compresses the valve prosthesis into the compressed configuration for delivery; and
   a radially-expandable sleeve secured to and encircling an outer surface of the valve prosthesis, wherein the radially-expandable sleeve has a delivery state in which the radially-expandable sleeve has a first diameter and extends over a full length of the valve prosthesis in the compressed configuration and a deployed state in which the radially-expandable sleeve has a second diameter greater than the first diameter and extends over a portion of the valve prosthesis in the expanded configuration, the portion being less than the full length of the valve prosthesis, the radially-expandable sleeve being configured to prevent paravalvular leakage in situ in the deployed state,
   wherein the radially-expandable sleeve is configured to contract longitudinally when the radially-expandable sleeve transforms from the delivery state to the deployed state.

13. The delivery system of claim 12, wherein the radially-expandable sleeve in the deployed state extends over only an inflow end portion of the valve prosthesis in the expanded configuration and lays flush against the outer surface of the valve prosthesis.

14. The delivery system of claim 12, wherein the radially-expandable sleeve is formed from an elastic material that is stretched over the valve prosthesis in the compressed configuration.

15. The delivery system of claim 12, further comprising at least one sleeve-restraining suture for coupling the radially-expandable sleeve to the delivery system, wherein the at least one sleeve-restraining suture is removable.

16. The delivery system of claim 15, wherein the at least one cinching suture is disposed between the outer surface of the valve prosthesis and an inner surface of the radially-expandable sleeve.

17. The delivery system of claim 15, wherein the at least one sleeve-restraining suture includes a first sleeve-restraining suture at a first end of the radially-expandable sleeve and a second sleeve-restraining suture at a second end of the radially-expandable sleeve.

\* \* \* \* \*